United States Patent [19]
Robertson et al.

[11] Patent Number: 5,942,430
[45] Date of Patent: Aug. 24, 1999

[54] ESTERASES

[75] Inventors: Dan E. Robertson, Haddonfield, N.J.; Dennis Murphy, Paoli; John Reid, Bryn Mawr, both of Pa.; Anthony M. Maffia; Steven Link, both of Wilmington, Del.; Ronald V. Swanson, Media, Pa.; Patrick V. Warren, Philadelphia, Pa.; Anna Kosmotka, Brookhaven, Pa.

[73] Assignee: Diversa Corporation, San Diego, Calif.

[21] Appl. No.: 08/602,359

[22] Filed: Feb. 16, 1996

[51] Int. Cl.$^6$ .............................. C12N 9/18; C12N 15/55
[52] U.S. Cl. ................. 435/197; 435/196; 435/252.3; 435/325; 435/320.1; 536/23.2
[58] Field of Search ........................... 536/23.2; 435/196, 435/197, 252.3, 325, 320.1

[56] References Cited

PUBLICATIONS

I.G. Kim et al., "Structure and Organization of the Human Transglutaminase 1 Gene", J. Biol. Chem. 267(11): 7710–7717, Apr. 1992.
GenBank entry X86487, Jan. 1996.

*Primary Examiner*—Rebecca E. Prouty
*Attorney, Agent, or Firm*—Fish & Richardson P.C.

[57] ABSTRACT

Esterase enzymes derived from various Staphylothermus, Pyrodictium, Archaeoglobus, Aquifex, M11TL, Thermococcus, Teredinibacter and Sulfolobus organisms are disclosed. The enzymes are produced from native or recombinant host cells and can be utilized in the pharmaceutical, agricultural and other industries.

9 Claims, 17 Drawing Sheets

FIG. 1
Staphylothermus Marinus - F1-12LC

```
  1 ATG TCT TTA AAC AAG CAC TCT TGG ATG GAT ATG ATA TTT ATT CTC AGC TTT TCT TTC   60
  1 Met Ser Leu Asn Lys His Ser Trp Met Asp Met Ile Ile Phe Ile Leu Ser Phe Ser Phe  20

61 CCA TTA ACA ATG ATC GCA TTA GCT ATC TCT ATG TCG TCA TGG TTT AAT ATA TGG AAT AAT  120
 21 Pro Leu Thr Met Ile Ala Leu Ala Ile Ser Met Ser Ser Trp Phe Asn Ile Trp Asn Asn  40

121 GCA TTA AGC GAT CTA GGA CAT GCT AAA AGC AGT GTT GCT CCA ATA TTC AAT CTA GGT  180
 41 Ala Leu Ser Asp Leu Gly His Ala Lys Ser Ser Val Ala Pro Ile Phe Asn Leu Gly  60

181 CCT GCA ATT GGT GGG ATA CTA ATT GTT GGT TTA AGA AAT CTT CTT TAT TCG TGG AGT  240
 61 Leu Ala Ile Gly Gly Ile Leu Ile Val Gly Leu Arg Asn Leu Leu Tyr Ser Trp Ser  80

241 AGA GTT AAA GGA TCT AAA GTT CTT ATA TCC ATG GGT GTA CTT CTT AAC TTA ATA GGG GTT TTC  300
 81 Arg Val Lys Gly Ser Leu Ile Ser Met Gly Val Phe Leu Asn Leu Ile Gly Val Phe  100

301 GAC GAA GTA TAT GGT TGG CTA GTC TCA GTC TTC TTT CTA GTT GTT TTC TTA TCA ATA ATA  360
101 Asp Glu Val Tyr Gly Trp Leu Val Ser Val Leu Phe Phe Leu Val Val Phe Leu Ser Ile Ile  120

361 GCA TAT TTC ATA AGT CTT GAC AAA TCA CTT TGC TCT GTT CTA GTT CTA CTA ATA ATA  420
121 Ala Tyr Phe Ile Ser Leu Asp Lys Ser Trp Ile Ala Val Leu Leu Ile Ile  140

421 GGT CAT ATT GCA ATG TGG TAT CTA CAC TTT GCT TCA GAG ATT CCG AGA GGT GCG GCT ATT  480
141 Gly His Ile Ala Met Trp Tyr Leu His Phe Ala Ser Glu Ile Pro Arg Gly Ala Ala Ile  160

481 CCC GAG TTA TTA GCG GTA TTC TCG TTT TTA CCA TTC TAT ATA AGA GAC TAT TTT AAA TCA  540
161 Pro Glu Leu Leu Ala Val Phe Ser Phe Leu Pro Phe Tyr Ile Arg Asp Tyr Phe Lys Ser  180

541 TAC ACT AAA CGA TAG  555
181 Tyr Thr Lys Arg End  185
```

FIG. 2A
Pyrodictium - TAG11-17LC

```
  1 ATG AAA CTC CTT GAG CCC ACA AAT ACC TCC TAC CAG GAT TTA GCA TTG CAT  60
  1 Met Lys Leu Leu Glu Pro Thr Asn Thr Ser Tyr Gln Asp Leu Ala Leu His  20

61 TTT GCA TTT TAC TGG TTT CTG GCC GTG TAT ACG TGG TTA CCC GGT GTC CGG GGC 120
 21 Phe Ala Phe Tyr Trp Phe Leu Ala Val Tyr Thr Trp Leu Pro Gly Val Arg Gly  40

121 GTA GCT GTG GAC ACA GGG GTG CCT GTG GCT CGG GTC GGG CTC GGG CGG GGT AAG AGG CTG 180
 41 Val Ala Val Asp Thr Gly Val Pro Val Ala Arg Val Gly Leu Gly Arg Arg Gly Lys Arg Leu  60

181 CTC CTG GCC GCT GTC TTG GCT GTC GTT GTT GTC CCG GCT TAT GTG 240
 61 Leu Leu Ala Ala Val Leu Ala Val Val Ser Val Val Pro Ala Tyr Val  80

241 GCG TAT AGT AGT CTG CAC CCG GAG AGC TGT CGG CCC GTT GCG CCC GAG GGG CTC ACC TAC 300
 81 Ala Tyr Ser Ser Leu His Pro Glu Ser Cys Arg Pro Val Ala Pro Glu Gly Leu Thr Tyr 100

301 AAA GAG TTC AGC GTG ACC GTG GCG GAT GGC TTG GTG GTT CGG GTG TGG CTG GGC CCC 360
101 Lys Glu Phe Ser Val Thr Val Ala Asp Gly Leu Val Val Arg Gly Trp Val Leu Gly Pro 120

361 GGC GCT GGG AAC CCG GTG TTC GTT TTG ATG CAC GGG TAT ACT GGG TGC TCG GCG 420
121 Gly Ala Gly Asn Pro Val Phe Val Leu Met His Gly Tyr Thr Gly Cys Ser Ala 140

421 CCC TAC ATG GCT GTG CTG GCC CGG GAG CTC GTG GAG TGG GGG TAC CCG GTT GTC TTC 480
141 Pro Tyr Met Ala Val Leu Ala Arg Glu Leu Val Glu Trp Gly Tyr Pro Val Val Phe 160

481 GAC TTC CGG GGC CAC AGC GGG GGC ACG ATT GGG CCC CGG GAG GTG CTG 540
161 Asp Phe Arg Gly His Ser Gly Gly Thr Ile Gly Pro Arg Glu Val Leu 180

541 GAT GCC CGG GCT GTG GGC TAT GTC TCG GAG CGG TTC CCC CGG CGG ATA ATA TTG 600
181 Asp Ala Arg Ala Val Gly Tyr Val Ser Glu Arg Phe Pro Gly Arg Ile Ile Leu 200
```

FIG. 2B
Pyrodictium - TAG11-17LC

```
601 GTG GGG TTC AGT ATG GGC GCT GTA GCG ATC GTG GAG GGT GCT GGG GAC CCG CGG GTC 660
201 Val Gly Phe Ser Met Gly Ala Val Ala Ile Val Glu Gly Ala Gly Asp Pro Arg Val 220

661 TAC GCG GTG GCT GAT AGC TAC TAT AGG CTC CGG GAC GTC ATA CCC CGG TGG CTG 720
221 Tyr Ala Val Ala Asp Ser Tyr Tyr Arg Leu Arg Asp Val Ile Pro Arg Trp Leu 240

721 GAG TAC AAG ACG CTG CCG GGC TGG CCG GGG TTC TAC GGG AGG CTG 780
241 Glu Tyr Lys Thr Leu Pro Gly Trp Pro Val Leu Ala Gly Phe Tyr Gly Arg Leu 260

781 ATG GCG GGC GTT GAC CTC GGC TTC GGG GTG GAT AAG CCG TTG 840
261 Met Ala Gly Val Asp Leu Gly Phe Gly Pro Ala Gly Val Glu Arg Val Asp Lys Pro Leu 280

841 CTG GTG TAT GGG CCC CGG GAC CCG CTG ACG GAG CGG AGC CTG GCG 900
281 Leu Val Val Tyr Gly Pro Arg Asp Pro Leu Val Thr Arg Asp Glu Ala Ser Leu Ala 300

901 TCC CGT AGC CCG TGT CTC GAG GTT CCT GGG GCT CAC GTG GAG GCC GTG 960
301 Ser Arg Ser Pro Cys Leu Glu Val Pro Gly Ala Gly His Val Glu Ala Val 320

961 GAT GTG CTG GGG CCG CGC GGC ATG ATG GAC CTG ATA GAG CTG GCG CAC GAG GAG TGC 1020
321 Asp Val Leu Gly Pro Arg Tyr Ala Asp Met Leu Ile Glu Leu Ala His Glu Glu Cys 340

1021 CCT CCG GGG GCC GGT GGC TGA
341 Pro Pro Gly Ala Gly Gly End
```
1041
347

FIG. 3A
Archaeoglobus Venificus SN P6-24LC

```
  1 ATG CCA TAT GTT AGG AAT GGT GTA AAT ATC TAT TAT GAA CTG GTG GAT GGA CCT GAG   60
  1 Met Pro Tyr Val Arg Asn Gly Val Asn Ile Tyr Tyr Glu Leu Val Asp Gly Pro Glu   20

61 CCA CCA ATT GTC TTT GTT CAC GGA TGG ACA GCA AAT ATG AAT TTT TGG AAA GAG CAA AGA  120
 21 Pro Pro Ile Val Phe Val His Gly Trp Thr Ala Asn Met Asn Phe Trp Lys Glu Gln Arg   40

121 CGT TAT TTT GCA GGC AGG AAT ATG TTG TTT GTC GAT AAC AGA GGT CAG GGC AGG TCC  180
 41 Arg Tyr Phe Ala Gly Arg Asn Met Leu Phe Val Asp Asn Arg Gly Gln Gly Arg Ser   60

181 GAT AAG CCA CTT GGA TAC GAT TTC TAC AGA TTT GAG AAC TTC ATT TCA GAT TTA GAT GCG  240
 61 Asp Lys Pro Leu Gly Tyr Asp Phe Tyr Arg Phe Glu Asn Phe Ile Ser Asp Leu Asp Ala   80

241 GTT GTT AGG GAG ACT GGA GTG GAG AAA TTT GTT CTC GTC GGA CAT TCA TTC GGA ACA ATG  300
 81 Val Val Arg Glu Thr Gly Val Glu Lys Phe Val Leu Val Gly His Ser Phe Gly Thr Met  100

301 ATC TCT ATG AAG TAC TGT TCG GAG TAT CGG AAT CGG GTT CTT GCT CTA ATC CTC ATA GGT  360
101 Ile Ser Met Lys Tyr Cys Ser Glu Tyr Arg Asn Arg Val Leu Ala Leu Ile Leu Ile Gly  120

361 GGT GGG AGC AGA ATA AAG CTT CTA CAC AGA ATT GGA TAT CCT TTA GCA AAG ATT CTT GCA  420
121 Gly Gly Ser Arg Ile Lys Leu Leu His Arg Ile Gly Tyr Pro Leu Ala Lys Ile Leu Ala  140

421 TCC ATT GCA TAC AAG AAG TCT CAA GAT TTG GTC GCA GAT CTT TCC TTT GGC AAA AAT GCT  480
141 Ser Ile Ala Tyr Lys Lys Ser Gln Asp Leu Val Ala Asp Leu Ser Phe Gly Lys Asn Ala  160

481 GGT GAA CTT AAA GAG TGG GGA TGG GAG TGG AAA CAG GCA ATG GAT ACA CCC TCC TAC GTG GCA  540
161 Gly Glu Leu Lys Glu Trp Gly Trp Lys Gln Ala Met Asp Thr Pro Ser Tyr Val Ala  180

541 ATG TAC ACG TAC AGA ACT CTA ACG AAA AAT CTT GAA AAT ATC TTG GAG AAA ATA GAC  600
181 Met Tyr Thr Tyr Arg Thr Leu Thr Lys Val Asn Leu Glu Asn Ile Leu Glu Lys Ile Asp  200

601 TGT CCA ACA CTG ATT GTT GGA GAG GAT GCA CTA TTG CCC GTT AGC GTT AGC TCA GTT  660
201 Cys Pro Thr Leu Ile Val Gly Glu Asp Ala Leu Leu Pro Val Ser Lys Ser Val  220
```

FIG. 3B
Archaeoglobus Veniificus SN P6-24LC

```
661 GAG CTG ACG AGG AGG ATA GAA AAC TCA AAG CTT GTG ATC ATC CCA AAC TCG GGG CAT TGC 720
221 Glu Leu Thr Arg Arg Ile Glu Asn Ser Lys Leu Val Ile Ile Pro Asn Ser Gly His Cys 240

721 GTA ATG CTT GAG AGT CCA AGT GAG GTT AAT AGA GCA ATG GAC GAA TTC ATT TCT TCA GCA 780
241 Val Met Leu Glu Ser Pro Ser Glu Val Asn Arg Ala Met Asp Glu Phe Ile Ser Ser Ala 260

781 CAG TTC TAA                                                                    789
261 Gln Phe End                                                                    263
```

FIG. 4
Aquifax pyrophilus - 28LC

```
  1 TTG AGA TTG AGG AAA TTT GAA GAG ATA AAC CTC GTT CTT TCG GGA GGA GCT GCA AAG GGC   60
  1 Leu Arg Leu Arg Lys Phe Glu Glu Ile Asn Leu Val Leu Ser Gly Gly Gly Ala Lys Gly   20

61 ATA GCC CAC ATA GGT GTT TTG AAA GCT ATA AAC GAG CTC GGT ATA AGG GTG AGG GCT TTA  120
 21 Ile Ala His Ile Gly Val Leu Lys Ala Ile Asn Glu Leu Gly Ile Arg Val Arg Ala Leu   40

121 AGC GGG GTG AGC GCC GGG GCA ATC GTT TCG GTC TTT TAT GCC TCA GGC TAC TCC CCT GAA  180
 41 Ser Gly Val Ser Ala Gly Ala Ile Val Ser Val Phe Tyr Ala Ser Gly Tyr Ser Pro Glu   60

181 GGG ATG TCC AGC CTT CTG AAG CTG AAC TGG GTA AAC TGG GTG CTG AAG CTG TTT AAG TTC AAG CCA CCT  240
 61 Gly Met Phe Ser Leu Leu Lys Leu Asn Trp Val Asn Trp Val Leu Lys Leu Phe Lys Pro Pro   80

241 CTG AAG GGA TTG ATA GGG TGG GAG AAG TTC CTT AGA ATT AGA TTC GAG GTT CTC CCT TAC  300
 81 Leu Lys Gly Leu Ile Gly Trp Glu Lys Ala Ile Arg Phe Leu Glu Val Leu Pro Tyr  100

301 AGG AGA ATA GAA AAA CTT GAG TAC CTC TCG GAA AGT TTA ATC CCC GCA CTT CTC GGC AGT TTA ATC CCC GCA CTT CTC GGC AGC TGT GCA ATT  420
121 Arg Arg Ile Glu Lys Leu Glu Tyr Leu Ser Glu Ser Leu Ile Pro Ala Leu Leu Gly Ser Cys Ala Ile  140

421 CCC GGC ATA TTT GAA CCC GTT GAG TAT AAG AAT TAC TTG CTC CTC GTT GAC GGA GGT ATA GTT  480
141 Pro Gly Ile Phe Glu Pro Val Glu Tyr Lys Asn Tyr Leu Leu Val Asp Gly Gly Ile Val  160

481 AAC AAC CTT CCC GTT GAG CCC GTT CAG GAA CCC TTT CAG GAA GGT ATT CCC ATT CTT CAC ATC TTG AGG AGC TTC  540
161 Asn Asn Leu Pro Val Glu Pro Phe Gln Glu Gly Ile Pro Thr Val Cys Val Asp Val  180

541 CTT CCC ATA GAG GTC CGC CGC TCA AAC TCC GAA AAG AGA ATA AAG AAG ATT CTT CAC ATC TTG AGG AGC TTC  600
181 Leu Pro Ile Glu Val Arg Arg Ser Asn Ser Glu Lys Arg Ile Lys Lys Ile Leu Leu Arg Ser Phe  200

601 TTT CTT GCG GTC CGC CGC TCA AAC TCC GAA AAG AGA AAG AAG AGA TTT TGT GAC TTC GTT ATA GTT  660
201 Phe Leu Ala Val Arg Ser Asn Ser Glu Lys Arg Lys Lys Arg Phe Cys Asp Leu Val Ile Val  220

661 CCT GAG GAG TTC ACA CCC CTT GAT GTT AGA GCG CAA ATA ATG GAG AGG  720
221 Pro Glu Glu Phe Thr Pro Leu Asp Val Arg Lys Ala Asp Gln Ile Met Glu Arg  240

721 GGA TAC ATA AAG GCC TTA GAG GTA CTT TCT GAA TAG  756
241 Gly Tyr Ile Lys Ala Leu Glu Val Leu Ser Glu End  252
```

FIG. 5A
M11TL-29L.

```
  1 ATG TTT AAT ATC AAT GTC TTT GTT AAT ATA TCT TGG CTG TAT TTT TCA GGG ATA GTT ATG   60
  1 Met Phe Asn Ile Asn Val Phe Val Asn Ile Ser Trp Leu Tyr Phe Ser Gly Ile Val Met   20

61 AAG ACT GTG GAA GAG TAT GCG CTA CTT GAA CTT GGA ACA GGC GTA AGA GTG TTT TAT CGG TGT GTA  120
 21 Lys Thr Val Glu Glu Tyr Ala Leu Leu Glu Leu Gly Thr Gly Val Arg Val Phe Tyr Arg Cys Val  40

121 ATC CCG GAG AAA GCT TTT AAC ACT TTG ATA ATA GGT TCA CAC GGA TTG GGG GCG CAC AGT  180
 41 Ile Pro Glu Lys Ala Phe Asn Thr Leu Ile Ile Gly Ser His Gly Leu Gly Ala His Ser  60

181 GGA ATC TAC ATT AGT GCT GAA TTT GTT GGA CAT AGG CAC GGA TTC TGC ATG GGC TTT  240
 61 Gly Ile Tyr Ile Ser Ala Glu Phe Val Gly His Arg His Gly Phe Cys Met Gly Phe  80

241 GAT CAA AGG GGA CAT GGG AGA ACG GCA AGC GAT AGA GGG TAT GTG GAG GGC TTT  300
 81 Asp Gln Arg Gly His Gly Arg Thr Ala Ser Asp Arg Gly Tyr Val Glu Gly Phe  100

301 CAC AAC TTC ATA GAG GAT ATG AAG GCC TTC TCC GAT TAT GCC AAG TGG CGC GTG GGT  360
101 His Asn Phe Ile Glu Asp Met Lys Ala Phe Ser Asp Tyr Ala Lys Trp Arg Val Gly  120

361 GAC GAA ATA ATA TTG CTA GGA CAC AGT ATG GGG CTC ATA GCG CTC TTA ACA GTT GCA  420
121 Asp Glu Ile Ile Leu Leu Gly His Ser Met Gly Leu Ile Ala Leu Leu Thr Val Ala  140

421 ACT TAT AAA GAA ATC GCC AAG GGA CTT GTT CTA AGC GTT CTA GCC CTC CAA ATC CCC TTA  480
141 Thr Tyr Lys Glu Ile Ala Lys Gly Leu Val Leu Ser Val Leu Ala Leu Gln Ile Pro Leu  160

481 ACC CCG GCT AGA AGA AGA TTG CCG CAG AAA CCA GAG GGT TTT CAA AGA GCA AAA GAT ATA GAA  540
161 Thr Pro Ala Arg Arg Arg Leu Pro Gln Lys Pro Glu Gly Phe Gln Arg Ala Lys Asp Ile Glu  180

541 ACC TTA CAA AGG AGA TTG CCG CAG AAA CCA GAG GGT TTT CAA AGA GCA AAA GAT ATA GAA  600
181 Thr Leu Gln Arg Arg Leu Pro Gln Lys Pro Glu Gly Phe Gln Arg Ala Lys Asp Ile Glu  200

601 TAC AGT CTG AGT ATA TCA GTC GTG GAC CTC AAG ATG ATT AAA GCA TCA TCT ATG  660
201 Tyr Ser Leu Ser Ile Ser Val Val Asp Leu Lys Met Ile Lys Ala Ser Ser Met  220

661 TTG TGG ACC ATA GCA GGG GAA ATT AAT ACT CCC GTC CTT ATT CAT GGG GAA AAA GAC  720
221 Phe Trp Thr Ile Ala Gly Glu Ile Asn Thr Pro Val Leu Ile His Gly Glu Lys Asp  240
```

FIG. 5B
M11TL-29L.

```
721 AAT GTC ATA CCT CCG GAG GCG AGC AAA AAA GCC TAC CAA TTA ATA CCT TCA TTC CCT AAA  780
241 Asn Val Ile Pro Pro Glu Ala Ser Lys Lys Ala Tyr Gln Leu Ile Pro Ser Phe Pro Lys  260

781 GAG TTG AAA ATA TAC CCC GAT CTT GGA CAC AAC TTG TTT GAA CCA GGC GCG GTG AAA  840
261 Glu Leu Lys Ile Tyr Pro Asp Leu Gly His Asn Leu Phe Glu Pro Gly Ala Val Lys  280

841 ATC GTC ACA GAC ATT GTA GAG TGG GTT AAG AAT CTA CCC AGG GAA AAT CCT TAA  894
281 Ile Val Thr Asp Ile Val Glu Trp Val Lys Asn Leu Pro Arg Glu Asn Pro End  298
```

FIG. 6A
Thermococcus CL-2-30LC

```
  1 ATG GAG GTT TAC AAG GCC AAA TTC GGA GCA AAG CTC GGC TGG GTT CTG GTT CAT   60
  1 Met Glu Val Tyr Lys Ala Lys Phe Gly Glu Ala Lys Leu Gly Trp Val Leu Val His  20

61 GGC CTC GGC GAG CAC AAG GCA AGA AGG TAT GGA CTG ATT AAG GAA CTC AAC TAT GCC GGC  120
 21 Gly Leu Gly Glu His Lys Gly Arg Arg Tyr Gly Leu Ile Lys Glu Leu Asn Tyr Ala Gly  40

121 TTT GGA GTT TAC ACC TTC GAC TGG CCC GGC AAG AGC CCG GGC AAG AGA GGG CAC  180
 41 Phe Gly Val Tyr Thr Phe Asp Trp Pro Gly Lys Ser Pro Gly Lys Arg Gly His  60

181 ACG AGC GTC GAG GCG ATG GAA ATC GAC ATC GTC ATC GAG ATC AGG GAG AAG  240
 61 Thr Ser Val Glu Ala Met Glu Ile Asp Ile Val Ile Glu Ile Arg Glu Lys  80

241 CCC TTC TTC GGC CAC AGC CTG GGT CTA ACT GTC TTA ACT AGG TAC GCT GAG ACG CGG  300
 81 Pro Phe Phe Gly His Ser Leu Gly Leu Thr Val Leu Thr Arg Tyr Ala Glu Thr Arg  100

301 CCC GAT AAA ATA CGG GGA TTA ATA GCT CTC CCT GCC CTC GCC CCG GAA ACG  360
101 Pro Asp Lys Ile Arg Gly Leu Ile Ala Leu Pro Ala Leu Ala Ser Pro Glu Thr  120

361 CCG GGC TTC ATG GTG GCC CTC GAA GTT CTT GGA AAG ATC GCC CCG GGA GTT GTT CTC  420
121 Pro Gly Phe Met Val Ala Leu Glu Phe Leu Gly Lys Ile Ala Pro Gly Val Val Leu  140

421 TCC AAC GGC ATA AAG GAC CTC GTC CGA GAA CTC TCG CAG AGG GAC AGG GAC GCC GTG AGG AGG TAC GTT  480
141 Ser Asn Gly Ile Lys Asp Leu Val Arg Glu Leu Ser Arg Arg Asp Arg Asp Ala Val Arg Arg Tyr Val  160

481 GAA GAC CCA CTC GTC CAC GAC AGG ATT TCG GCC AAG CTG GGA AGG AGC ATC TTC GTG AAC  540
161 Glu Asp Pro Leu Val His Asp Arg Ile Ser Ala Lys Leu Gly Arg Ser Ile Phe Val Asn  180

541 ATG GAG CTG GCC CAC AGG GCG GAG GAC GCG AAA ATA AAA GTC CCG ATC CTT CTG ATG GGC  600
181 Met Glu Leu Ala His Arg Ala Glu Asp Ala Lys Ile Lys Val Pro Ile Leu Leu Met Gly  200

601 ACT GGC GAT GTA ATA ACC CGC AGA CTC TTC GAA GGC TCA CGG AGG CTG TTC GAG CTG GCC GTC  660
201 Thr Gly Asp Val Ile Thr Arg Arg Leu Phe Glu Gly Ser Arg Arg Leu Phe Glu Leu Ala Val  220

661 GAG AAC AAA ACC CTG AGA GTT CAC GAG GGC TAC CAC GAG ATA TTT GAA GAC CCC GAG  720
221 Glu Asn Lys Thr Leu Arg Val His Glu Gly Tyr His Glu Ile Phe Glu Asp Pro Glu  240
```

FIG. 6B
Thermococcus CL-2-30LC

```
721 TGG GCC GAG GAG TTC CAC GAA ACA ATT GTT AAG TGG CTG GTT GAA AAA TCG TAC TCT TCG  780
241 Trp Ala Glu Glu Phe His Glu Thr Ile Val Lys Trp Leu Val Glu Lys Ser Tyr Ser Ser  260

781 GCT CAA TAA  789
261 Ala Gln End  263
```

FIG. 7
Aquifex VF5-34LC

```
  1 TTG ATT GGC AAT TTG AAG AGG TTT GAA GAG GTT AAC TTA GTT CTT TCG GGA GGG   60
  1 Leu Ile Gly Asn Leu Lys Arg Phe Glu Glu Val Asn Leu Val Leu Ser Gly Gly   20

61 GCT GCC AAG GGT ATC GCC CAT ATA GGT GTT TTA AAA GCT CTG GAA GAG CTC GTT ATA AAG  120
 21 Ala Ala Lys Gly Ile Ala His Ile Gly Val Leu Lys Ala Leu Glu Glu Leu Gly Ile Lys   40

121 GTA AAG AGG CTC AGC GGG GTA AGT GCT GGA GCT ATC GTT TCC GTC TTT TAC GCT TCG GGC  180
 41 Val Lys Arg Leu Ser Gly Val Ser Ala Gly Ala Ile Val Ser Val Phe Tyr Ala Ser Gly   60

181 TAC ACT CCC GAC GAG ATG TTA AAA CTC CTG AAA GAG GTA AAC TGG GTA AAC TTT TTT AAG  240
 61 Tyr Thr Pro Asp Glu Met Leu Lys Leu Leu Lys Glu Val Asn Trp Val Asn Phe Phe Lys   80

241 TTC AAA ACA CCG AAA ATG GGC TTA ATG GGG TGG GAG AAG GCT GCA GCT GAG TTT TTG GAA AAA  300
 81 Phe Lys Thr Pro Lys Met Gly Leu Met Gly Trp Glu Lys Ala Ala Ala Glu Phe Leu Glu Lys  100

301 GAG CTC GGA GTT AAG AGG CTG GAA GAC CTG AAC ATA CCA ACC TAT CTT TGC TCG GCG GAT  360
101 Glu Leu Gly Val Lys Arg Leu Glu Asp Leu Asn Ile Pro Thr Tyr Leu Cys Ser Ala Asp  120

361 CTG TAC ACG GGA AAG GCT CTT TAC TTC GGC AGA GGT TTA CTT GAC TTA ATT CCC GTG CTT CTC GGA  420
121 Leu Tyr Thr Gly Lys Ala Leu Tyr Phe Gly Arg Gly Asp Leu Ile Pro Val Leu Leu Gly  140

421 AGT TGT TCC ATA CCC GGG ATT TTT GAA GTT GAG TAC GAG AAT TTT CTA CTT GTT GAC  480
141 Ser Cys Ser Ile Pro Gly Ile Phe Glu Val Glu Tyr Glu Asn Phe Leu Leu Val Asp  160

481 GGA GGT ATA GTG AAC AAC CTG CCC GTA GAA CCT TTG GAA AAG TTC AAA GAA CCC ATA ATC  540
161 Gly Gly Ile Val Asn Asn Leu Pro Val Glu Pro Leu Glu Lys Phe Lys Glu Pro Ile Ile  180

541 GGG GTA GAT GTG CTT CTG CCC ATA ACT CAA GAA ATT AAA AAT ATA CTC CAC ATC CTT  600
181 Gly Val Asp Val Leu Pro Ile Thr Gln Glu Ile Lys Asn Ile Leu His Ile Leu  200

601 ATA AGG AGC TTC TTT CTG GCG GTT CGT GTT TCC AAT TCG GAA AAG AGA AAG GAG TTC TGC AAC  660
201 Ile Arg Ser Phe Phe Leu Ala Val Arg Ser Asn Ser Glu Lys Arg Lys Glu Phe Cys Asn  220

661 GTA GTT ATA GAA CCT CCC CTT GAA GAG TTC TCT CTG GAC GTA AAT AAG GCG GAC GAG  720
221 Val Val Ile Glu Pro Leu Glu Glu Phe Ser Pro Leu Asp Val Asn Lys Ala Asp Glu  240

721 ATA TTC TGC GGG GAT ATG AGA GCA CTT TAA   750
241 Ile Phe Cys Gly Asp Met Arg Ala Leu End    250
```

FIG. 8A
Teredinibacter - 42L

```
  1 ATG CCA GCT AAT GAC TCA CCC ACG ATC GAC TTT AAT CCT CGC GGC ATT CTT CGC AAC GCT   60
  1 Met Pro Ala Asn Asp Ser Pro Thr Ile Asp Phe Asn Pro Arg Gly Ile Leu Arg Asn Ala   20

61 CAC GCA CAG GTT ATT TTA GCG ACT TCC GGC TTG CGC AAA GCG TTT TTG AAA CGC ACG CAC  120
 21 His Ala Gln Val Ile Leu Ala Thr Ser Gly Leu Arg Lys Ala Phe Leu Lys Arg Thr His   40

121 AAG AGC TAC CTC AGC GCC CAA TGG CTG CAG TGG CTG GAG CTC GAT GCC GGC AAC GGA GTT ACC TTG  180
 41 Lys Ser Tyr Leu Ser Ala Gln Trp Leu Glu Leu Asp Ala Gly Asn Gly Val Thr Leu   60

181 GCC GGA GAG CTT AAC ACA GCG CCT GCA ACT GCA TCC TCC CAC CCG GCG CAC AAG AAC TCC  240
 61 Ala Gly Glu Leu Asn Thr Ala Pro Ala Thr Ala Ser Ser His Pro Ala His Lys Asn Ser   80

241 ACT CTG GTT ATT GTG CAC GGC GAA GGC TCC AGC TCC CAG TCG GCC TAT GCG ACC TCC  300
 81 Thr Leu Val Ile Val His Gly Glu Gly Ser Ser Gln Ser Ala Tyr Ala Thr Ser  100

301 GCT GGC AGC ACG CTT TTC GAC CTT TTT CGC ACT TTT AAC TTC CGC CTT AAT TTT CGC GAT CAC  360
101 Ala Gly Ser Thr Leu Phe Asp Leu Phe Arg Thr Phe Asn Phe Arg Leu Asn Phe Arg Asp His  120

361 GGC GAC ACC TAC AAA GCC TAC CAC CAA TTA AAC CGC CAA ACC TAC GAC AAG TAT TGC CTG ATT GAC TAT TGC CTG ATG GGG TTC  420
121 Gly Asp Thr Tyr Lys Ala Tyr His Gln Leu Asn Arg Gln Thr Tyr Asp Lys Tyr Cys Leu Met Gly Phe  140

421 GGC GCA GTC AAA GCC TTT GCC TTG CGC CAG CAT CTC GCC GAA CAG CAC CAC ACC ATG AAA CCG  480
141 Gly Ala Val Lys Ala Phe Ala Leu Arg Gln His Leu Ala Glu Gln His His Thr Lys Pro  160

481 TCA CTT GGT GGG AAC TTT GCC ATC GCC GTC CTG CGG GAA CAG CAT CAC ACC ATG ATG GCC CTA  540
161 Ser Leu Gly Gly Asn Phe Ala Ile Ala Val Leu Arg Glu Gln His His Thr Met Met Ala Leu  180

541 CTA GCG GGC GTG CTC GTA TGC GCC TAT TTT GCG CAT AAA TGG AAG CGC TTA ACC  600
181 Leu Ala Gly Val Leu Val Cys Ala Tyr Phe Ala His Lys Trp Lys Arg Leu Thr  200

601 AAC CGA GGT GGC TTT TTC TAC CGC GGC TAC TTT GCG CAT AAA TGG AAG CGC TCG TTA ACC  660
201 Asn Arg Gly Gly Phe Phe Tyr Arg Gly Tyr Phe Ala His Lys Trp Lys Arg Ser Leu Thr  220

661 GCA AAA CTT GCA GCT TTC CCA GAC GCT TTC GGA AAA TAC GGC AAA GAT TTA AAA TCG ATA CAC ACG  720
221 Ala Lys Leu Ala Ala Phe Pro Asp Tyr Phe Gly Lys Tyr Gly Lys Asp Leu Lys Ser Ile His Thr  240
```

FIG. 8B
Teredinibacter - 42L

```
721 CTT GAT GAG TTA AAC AAC TAT TTC ATT CCC CGC TAC ACC GGC TTC AAC TCA GTC TCC GAA  780
241 Leu Asp Glu Leu Asn Asn Tyr Phe Ile Pro Arg Tyr Thr Gly Phe Asn Ser Val Ser Glu  260

781 TAC TTC AAA AGT TAC ACG CTC ACC GGG CAG AAG CTC GCG TTT CTC AAC TGC CCC AGT TAC  840
261 Tyr Phe Lys Ser Tyr Thr Leu Thr Gly Gln Lys Leu Ala Phe Leu Asn Cys Pro Ser Tyr  280

841 ATT CTG GCA GCT GGC GAC CCA ATA ATT CCA GCA TCC GAC TTT CAG AAA ATA GCC AAG  900
281 Ile Leu Ala Ala Gly Asp Pro Ile Ile Pro Ala Ser Asp Phe Gln Lys Ile Ala Lys  300

901 CCT GCG AAT CTG CAC ATA ACA CAA GGT TCT CAT TGC GCA TAC CTG GAA AAC  960
301 Pro Ala Asn Leu His Ile Thr Val Thr Gln Gly Ser His Cys Ala Tyr Leu Glu Asn  320

961 CTG CAT AAA CCT AGT GCT GCC GAC AAA TAT GCG GTG AAA TTA TTT GGA GCC TGT TGA  1017
321 Leu His Lys Pro Ser Ala Ala Asp Lys Tyr Ala Val Lys Leu Phe Gly Ala Cys End  339
```

FIG. 9A
Archeoglogus fulgidas VC16 - 16MC1

```
ATG CTT GAT ATG CCA ATC GAC CCT GTT TAC TAC CAG CTT GCT GAG TAT
Met Leu Asp Met Pro Ile Asp Pro Val Tyr Tyr Gln Leu Ala Glu Tyr
 1               5                  10                 15

TTC GAC AGT CTG CCG AAG TTC CAG TTT TCC TCG GCC AGA GAG TAC
Phe Asp Ser Leu Pro Lys Phe Gln Phe Ser Ser Ala Arg Glu Tyr
         20                  25                  30

AGG GAG GCG ATA AAT CGA ATA TAC GAG GTT AGA AAC CGG CAG AGC
Arg Glu Ala Ile Asn Arg Ile Tyr Glu Val Arg Asn Arg Gln Ser
         35                  40                  45

CAG CAT GAG GAC GTT GAA AGA GTT GAG GAC AGG ACG ATT AAG AGG
Gln His Glu Asp Val Glu Arg Val Glu Asp Arg Thr Ile Lys Arg
         50                  55                  60

AAC GGA ATC GTC AGA TAC CAG CAG TTT GGA CCC GAT CCG
Asn Gly Ile Val Arg Arg Tyr Gln Gln Phe Gly Pro Asp Pro
         65                  70        75           80

GGT CTG GTT TAC TTA TGC TAT GGA AYY CTT TGC ATC ACC
Val Leu Val Tyr Leu Cys Tyr Gly Ile Ile Leu Cys Ile Thr
         85                  90        95

TCG GAC GCC TTA GAT TGC TAC AGA AGG GCT CAC CCC
Ser Asp Ala Leu Asp Cys Tyr Arg Arg Ala Glu His Pro Ala
         100                 105                110

GTA GTC TCC GTG CCT TAC TAC AGG TGG ATC TTC AAC CGG
Val Ser Val Pro Leu Ala Tyr Tyr Arg Trp Ile Phe Asn Arg
         115                 120       125

CCA GTT TAT CAT AAG GCA ACC AAA CTT GCT GAG GGG GAC AGT
Ala Val Tyr Asp Lys Ala Thr Lys Val Ala Glu Gly Asp Ser
         130                 135       140

GAG GAG CTG AGG CCG TCA CTT ATA ATG GCC AGA GAC AGC
Glu Glu Leu Arg Pro Ser Val Ile Met Ala Arg Asp Ser
         145                 150       155         160

GCG GGA CGG AAT CTT GCC CCG GCG ATA
Ala Gly Arg Asn Leu Ala Ala Pro Ala Ile
165                 170        175
```

FIG. 9B
*Archeoglogus fulgidas VC16 - 16MC1*

```
GGA GAA GAT TTC ATA AAG CAT GAA ATT CTA ACT TAC CCC GTT GTG AAC
Gly Glu Asp Phe Ile Lys His Gln Ile Leu Ile Tyr Pro Val Val Asn
            180                 185             190

TTT GTA GCC CCC ACA CCA TCG CTT CTG TGG GAG TTT GGA GGG CTG TGG
Phe Val Ala Pro Thr Pro Ser Leu Leu Trp Glu Phe Gly Gly Leu Trp
        195             200             205

ATT CTC GAC GAC CAG ATA ATG AGT TTC TCG GAG CAG TAC TTC TCC
Ile Leu Asp Asp Gln Ile Met Ser Phe Ser Glu Gln Tyr Phe Ser
        210             215             220 (approx)

AGA GAG GAA GAT AAG AAG TTC CCC TCC GCC TCC GTA ATC GAA ATC GAC
Arg Glu Glu Asp Lys Lys Phe Pro Ser Ala Ser Val Ile Glu Ile Asp
235                 240             245             250

CTT AAC CTA CCT GTT CTG CCC TCC ACC ATA GCC GAA AGA CAC ATA GCG
Leu Asn Leu Pro Val Leu Pro Ser Thr Ile Ala Glu Arg His Ile Ala
    255             260             265

CTG GAT GAA GTT GGA GAA GTT CTG GGG TTT CAG ATG CTG ATG ATG CCG GGT
Leu Asp Glu Val Gly Glu Val Leu Gly Phe Gln Met Leu Leu Met Pro Gly
        270             275             280

GTT GAG GCG AGC ATC GTC TAC AGA TAC AGA GGA GTG AGG GCC ATC
Val Glu Ala Ser Ile Val Tyr Arg Tyr Arg Gly Val Arg Ala Ile
    285             290             295

AAT TAC TAT CTG CTG CCC GTG CTG AAG GCT GCG AGG GAT CCG ATA AAC
Asn Tyr Tyr Leu Leu Pro Val Leu Lys Ala Ala Arg Asp Pro Ile Asn
300         305                 310

GCC CTT CTT GTT GTG TTC GAC TAG
Ala Leu Leu Val Val Phe Asp ***
315             320
```

FIG. 10A
Sulfolobus Solfatarious P1 8LC1

```
ATG CCC CTA GAT CCT AGA ATT AAA AAG TTA CTA GAA TCA GCT CTT ACT
Met Pro Leu Asp Pro Arg Ile Lys Lys Leu Leu Glu Ser Ala Leu Thr
 1                5              10              15

ATA CCA ATT GGT AAA GCC CCA GTA GAA GAG GTA AAG AGA AAG ATA TTT AGG
Ile Pro Ile Gly Lys Ala Pro Val Glu Glu Val Lys Arg Lys Ile Phe Arg
                20              25              30

CAA TTA GCG TCG GCA GCT GCC CCC AAA GTC GAA GTT ATA AAC GCT AGA GTA GAA GAT
Gln Leu Ala Ser Ala Ala Pro Lys Val Glu Val Ile Asn Ala Arg Val Glu Asp
        35              40              45

ATA AAA ATA CCA GGC AGT GAA ACC GGT TAT GTG TGC AAG CTT CAT TAT TTT
Ile Lys Ile Pro Gly Ser Glu Thr Gly Tyr Val Cys Lys Leu His Tyr Phe
    50              55              60

CCG AAG AGT AGC GGT CCT TAT GAA GTT TCT GTA CCA TTA TGT GGA GGC
Pro Lys Ser Ser Gly Pro Tyr Glu Val Ser Val Pro Leu Cys Gly Gly
65              70              75      80

GGT TTT GTA ATA GGC GAT GGC GTT TCA GAC GTA ATC GAT TCA AGA GCA
Gly Phe Val Ile Gly Asp Gly Val Ser Asp Val Ile Asp Ser Arg Ala
        85              90              95

ATT ACA AAT GCG TAC AAT TGC AAG TAT GTA GTA TCA GAT TCA GGA TTA
Ile Thr Asn Ala Tyr Asn Cys Lys Tyr Val Val Ser Asp Ser Gly Leu
    100             105             110

GCT CCA GAA TGG CCA GTT CCT TCT GCA TTA GAT GTT ATC GAT TTT GAC GCT
Ala Pro Glu Trp Pro Val Pro Ser Ala Leu Asp Val Ile Asp Phe Asp Ala
115             120             125

ACT AAT TAT TAT AAC TTT AAC TTA GAT AAA TTT GGA AAG ATG GGA
Thr Asn Tyr Tyr Asn Phe Asn Leu Asp Lys Phe Gly Lys Met Gly
130             135             140

GTT GCG GAT AGT GCT GGA AAT TTG GCA GCG GTT GTA
Val Ala Asp Ser Ala Gly Asn Leu Ala Ala Val Val
145             150             155     160
```

FIG. 10B
Sulfolobus Solfatarious P1 8LC1

```
GCT CTT CTT TCA AAG GGT AAA ATT AAT TTG AAG TAT CAA ATA CTG GTT
Ala Leu Leu Ser Lys Gly Lys Ile Asn Leu Lys Tyr Gln Ile Leu Val
                165                 170                 175

TAC CCA GCG GTA AGT TTA GAT AAC GTT TCA AGA TCC ATG ATA GAG TAC
Tyr Pro Ala Val Ser Leu Asp Asn Val Ser Arg Ser Met Ile Glu Tyr
            180                 185                 190

TCT GAT GGG TTC TTC CTT ACC AGA GAG CAT ATA TTG GAC TTT AGG TTC
Ser Asp Gly Phe Phe Leu Thr Arg Glu His Ile Leu Asp Phe Arg Phe
        195                 200                 205

GGT TCT CAA TAC TTA CGA AGC CCT GCA GAT TTG CTA CCA GAC TTT TCT
Gly Ser Gln Tyr Leu Arg Ser Pro Ala Asp Leu Leu Pro Asp Phe Ser
    210                 215                 220

ATT CTG GCG CAA GAT GCC TTC AAC GGA TTA CCT CCA GCC TAT TTT TTC
Ile Leu Ala Gln Asp Ala Phe Asn Gly Leu Pro Pro Ala Tyr Phe Phe
225                 230                 235                 240

GCA GAA TAC GAT AGT CCA GTA AGG CAA GAT GAG GCG GCA AGA AAT AAC
Ala Glu Tyr Asp Ser Pro Val Arg Gln Asp Glu Ala Ala Arg Asn Asn
                245                 250                 255

CTA CTA CAA GGA TCA GTT GTC ACT AGT GTG AGA GAG ATG GAA CAA AAC
Leu Leu Gln Gly Ser Val Val Thr Ser Val Arg Glu Met Glu Gln Asn
            260                 265                 270

ATA CAC GGA TTC CTC TTC TCA TTG TTT ATG CCG CTT TTG AGA GGA GTT
Ile His Gly Phe Leu Phe Ser Leu Phe Met Pro Leu Leu Arg Gly Val
        275                 280                 285

GCT ATA GGT CTG ATA GGG TCT GTA CGA GTA TTT TAT AGA GAT AAA GAT
Ala Ile Gly Leu Ile Gly Ser Val Arg Val Phe Tyr Arg Asp Lys Asp
    290                 295                 300

ATT
Ile
305

TAA
```

ESTERASES

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as esterases. Esterases are enzymes that catalyze the hydrolysis of ester groups to organic acids and alcohols.

Many esterases are known and have been discovered in a broad variety of organisms, including bacteria, yeast and higher animals and plants. A principal example of esterases are the lipases, which are used in the hydrolysis of lipids, acidolysis(replacement of an esterified fatty acid with a free fatty acid) reactions, transesterification(exchange of fatty acids between triglycerides)reactions, and in ester synthesis. The major industrial applications for lipases include: the detergent industry, where they are employed to decompose fatty materials in laundry stains into easily removable hydrophilic substances; the food and beverage industry where they are used in the manufacture of cheese, the ripening and flavoring of cheese, as antistaling agents for bakery products, and in the production of margarine and other spreads with natural butter flavors; in waste systems; and in the pharmaceutical industry where they are used as digestive aids.

The polynucleotides and polypeptides of the present invention have been identified as esterases as a result of their enzymatic activity.

In accordance with one aspect of the present invention, there are provided novel enzymes, as well as active fragments, analogs and derivatives thereof.

In accordance with another aspect of the present invention, there are provided isolated nucleic acid molecules encoding the enzymes of the present invention including mRNAs, cDNAs, genomic DNAs as well as active analogs and fragments of such enzymes.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said enzymes and subsequent recovery of said enzymes.

In accordance with yet a further aspect of the present invention, there is provided a process for utilizing such enzymes, or polynucleotides encoding such enzymes for hydrolyzing ester groups to yield an organic acid and an alcohol. The esterases of the invention are stable at high temperatures and in organic solvents and, thus, are superior for use in production of optically pure chiral compounds used in pharmaceutical, agricultural and other chemical industries.

In accordance with yet a further aspect of the present invention, there are also provided nucleic acid probes comprising nucleic acid molecules of sufficient length to hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms by using certain regions, i.e., conserved sequence regions, of the nucleotide sequence.

These and other aspects of the present invention should be apparent to those skilled in the art from the teachings herein.

The following drawings are illustrative of embodiments of the invention and are not meant to limit the scope of the invention as encompassed by the claims.

FIG. 1 is an illustration of the full-length DNA (SEQ ID NO:23) and corresponding deduced amino acid sequence (SEQ ID NO:33) of *Staphylothermus marinus* F1-12LC of the present invention. Sequencing was performed using a 378 automated DNA sequencer (Applied Biosystems, Inc.) for all sequences of the present invention.

FIGS. 2A and 2B are an illustration of the full-length DNA (SEQ ID NO:24) and corresponding deduced amino acid sequence (SEQ ID NO:34) of Pyrodictium TAGI 1-17LC.

FIGS. 3A and 3B are an illustration of the full-length DNA (SEQ ID NO:25) and corresponding deduced amino acid sequence (SEQ ID NO:35) of *Archaeoglobus venificus* SNP6-24LC.

FIG. 4 is an illustration of the full-length DNA (SEQ ID NO:26) and corresponding deduced amino acid sequence (SEQ ID NO:36) of *Aquifex pyrophilus*-28LC.

FIGS. 5A and 5B are an illustration of the full-length DNA (SEQ ID NO:27) and corresponding deduced amino acid sequence (SEQ ID NO: 37) of M11TL-29L.

FIGS. 6A and 6B are an illustration of the full-length DNA (SEQ ID NO:28) and corresponding deduced amino acid sequence (SEQ ID NO:38) of Thermococcus CL-2-30LC.

FIG. 7 is an illustration of the full-length DNA (SEQ ID NO:29) and corresponding deduced amino acid sequence (SEQ ID NO:39) of Aquifex VF5-34LC.

FIGS. 8A and 8B are an illustration of the full-length DNA (SEQ ID NO:30) and corresponding deduced amino acid sequence (SEQ ID NO:40) of Teredinibacter-42L.

FIGS. 9A and 9B are an illustration of the full-length DNA (SEQ ID NO:31) and corresponding deduced amino acid sequence (SEQ ID NO:41) of *Archaeoglobus fulgidus* VC16-16MC.

FIGS. 10A and 10B are an illustration of the full-length DNA (SEQ ID NO:32) and corresponding deduced amino acid sequence (SEQ ID NO:42) of *Sulfolobus solfataricus* P1-8LC.

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences.

In accordance with an aspect of the present invention, there are provided isolated nucleic acids (polynucleotides)

which encode for the mature enzymes having the deduced amino acid sequences of FIGS. 1–10 (SEQ ID NOS:23–32).

The deposit(s) have been made under the terms of the Budapest Treaty on the International Recognition of the deposit of micro-organisms for purposes of patent procedure. The strains will be irrevocably and without restriction or condition released to the public upon the issuance of a patent. These deposits are provided merely as convenience to those of skill in the art and are not an admission that a deposit would be required under 35 U.S.C. §112. The sequences of the polynucleotides contained in the deposited materials, as well as the amino acid sequences of the polypeptides encoded thereby, are controlling in the event of any conflict with any description of sequences herein. A license may be required to make, use or sell the deposited materials, and no such license is hereby granted.

The polynucleotides of this invention were originally recovered from genomic gene libraries derived from the following organisms:

*Staphylothermus marinus* F1 is a thermophilic sulfur archaea which was isolated in Vulcano, Italy. It grows optimally at 85° C. ($T_{max}$=98° C.) at pH 6.5.

Pyrodictium TAG11 is a thermophilic sulfur archaea which was isolated in the Middle Atlantic Ridge. It grows optimally at 103° C. ($T_{max}$=110° C.) at pH 6.5.

*Archaeoglobus venificus* SNP6 was isolated in the Middle Atlantic Ridge and grows optimally at 75° C. ($T_{max}$=92° C.) at pH 6.9.

*Aquifex pyrophilus* KOI 5a was isolated at Kolbeinsey Ridge, North of Iceland. This marine organism is a gram-negative, rod-shaped, strictly chemolithoautrophic, knall gas bacterium. It grows optimally at 85° C. ($T_{max}$=95° C.) at pH 6.8.

M11TL is a new species of Desulfurococcus which was isolated from Diamond Pool (formerly Jim's Black Pool) in Yellowstone. The organism grows heterotrophically by fermentation of different organic materials (sulfur is not necessary) in grape-like aggregates optimally at 85–88° C. in a low salt medium at pH 7.0.

Thermococcus CL-2 was isolated in the North Cleft Segment of the Juan de Fuca Ridge from a severed alvinellid worm residing on a "black smoker" sulfide structure. This marine archaea forms pleomorphic cocci, and grows optimally at 88° C.

Aquifex VF5 was isolated at a beach in Vulcano, Italy. This marine organism is a gram-negative, rod-shaped, strictly chemolithoautotrophic, knall gas bacterium. It grows optimally at 85° C. ($T_{max}$=95° C.) at pH 6.8.

Teredinibacter (pure) is an endosymbiont of the shipworm *Bankia gouldi*. The organism has straight to slightly bent 5–10 μm rods, and forms spiral cells as stationary phase is met. The organism was described in Science (1983) 22:1401–1403. It grows optimally at 30° C. at pH 8.0.

*Archaeoglobus fulgidus* VC16 was isolated in Vulcano, Italy. The organism grows optimally at 85° C. ($T_{max}$=92° C.) at pH 7.0.

*Sulfolobus solfataricus* P1 grows optimally at 85° C. ($T_{max}$=87° C.) at pH 2.0.

Accordingly, the polynucleotides and enzymes encoded thereby are identified by the organism from which they were isolated, and are sometimes hereinafter referred to as F1/12LC (FIG. 1 and SEQ ID NOS:23 and 33), TAG11/17LC (FIG. 2 and SEQ ID NOS:24 and 34), SNP6/24LC (FIG. 3 and SEQ ID NOS:25 and 35), AqP/28LC (FIG. 4 and SEQ ID NOS:26 and 36), MlITL/29L (FIG. 5 and SEQ ID NOS:27 and 37), CL-2/30LC (FIG. 6 and SEQ ID NOS:28 and 38), VF5/34LC (FIG. 7 and SEQ ID NOS:29 and 39), Trb/42L (FIG. 8 and SEQ ID NOS:30 and 40), VC16/16MC (FIG. 9 and SEQ ID NOS:31 and 41) and P1/8LC (FIG. 10 and SEQ ID NOS: 32 and 42).

The polynucleotides and polypeptides of the present invention show identity at the nucleotide and protein level to known genes and proteins encoded thereby as shown in Table 1.

TABLE 1

| Enzyme | Gene w/closest Homology (Organism) | Protein Similarity (%) | Protein Identity (%) | DNA Identity (%) |
|---|---|---|---|---|
| F1/12LC | No significant homology | — | — | — |
| TAG11/17LC | No significant homology | — | — | — |
| SNP6/24LC | PIR S34609 - carboxylesterase Pseudomones sp. (strain KWI-56) open reading frame of unknown function in E. coli. | 46 | 27 | 42 |
| AqP/29LC | | 53 | 31 | 38 |
| M11TL/29LC | No significant homology | — | — | — |
| CL02/30LC | No significant homology | — | — | — |
| VF5/34LC | Identified by homology to 28LC; also homologous to ORF of unknown function 5' of tgs in E. coli | 84 | 71 | 71 |
| Trb/42L | No significant homology | — | — | — |
| P1-8LC | | | | |
| VC16-16MC | | | | |

All the clones identified in Table 1 encode polypeptides which have esterase activity.

This invention, in addition to the isolated nucleic acid molecules encoding the enzymes of the present invention, also provides substantially similar sequences. Isolated nucleic acid sequences are substantially similar if: (i) they are capable of hybridizing under conditions hereinafter described, to the polynucleotides of SEQ ID NOS:23–32; (ii) or they encode DNA sequences which are degenerate to the polynucleotides of SEQ ID NOS:23–32. Degenerate DNA sequences encode the amino acid sequences of SEQ ID NOS:33–42, but have variations in the nucleotide coding sequences. As used herein, substantially similar refers to the sequences having similar identity to the sequences of the instant invention. The nucleotide sequences that are substantially the same can be identified by hybridization or by sequence comparison. Enzyme sequences that are substantially the same can be identified by one or more of the following: proteolytic digestion, gel electrophoresis and/or microsequencing.

One means for isolating the nucleic acid molecules encoding the enzymes of the present invention is to probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated by one skilled in the art that the polynucleotides of SEQ ID NOS:23–32, or fragments thereof (comprising at least 12 contiguous nucleotides), are particularly useful probes. Other particularly useful probes for this purpose are hybridizable fragments of the sequences of SEQ ID NOS:1–22 (i.e., comprising at least 12 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9 M NaCl, 50 mM NaH$_2$PO$_4$, pH 7.0, 5.0 mM Na$_2$EDTA, 0.5 % SDS, 10×Denhardt's, and 0.5 mg/mL polyriboadenylic acid. Approximately 2×10$^7$ cpm (specific activity 4–9×10$^8$ cpm/ug) of $^{32}$P end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM Na$_2$EDTA) containing 0.5% SDS, followed by a 30 minute wash in fresh 1×SET at Tm $^-$10° C. for the oligo-nucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. See J. Sambrook et al., *Molecular Cloning, A Laboratory Manual*, 2d Ed., Cold Spring Harbor Laboratory (1989) which is hereby incorporated by reference in its entirety.

As used herein, a first DNA (RNA) sequence is at least 70% and preferably at least 80% identical to another DNA (RNA) sequence if there is at least 70% and preferably at lest a 80% or 90% identity, respectively, between the bases of the first sequence and the bases of the another sequence, when properly aligned with each other, for example when aligned by BLASTN.

The present invention relates to polynucleotides which differ from the reference polynucleotide such that the changes are silent changes, for example the change do not alter the amino acid sequence encoded by the polynucleotide. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

The polynucleotides of this invention were recovered from genomic gene libraries from the organisms listed in Table 1. Gene libraries were generated in the Lambda ZAP II cloning vector (Stratagene Cloning Systems). Mass excisions were performed on these libraries to generate libraries in the pBluescript phagemid. Libraries were generated and excisions were performed according to the protocols/methods hereinafter described.

The polynucleotides of the present invention may be in the form of RNA or DNA which DNA includes cDNA, genomic DNA, and synthetic DNA. The DNA may be double-stranded or single-stranded, and if single stranded may be the coding strand or non-coding (anti-sense) strand. The coding sequences which encodes the mature enzymes may be identical to the coding sequences shown in FIGS. 1–10 (SEQ ID NOS:23–32) or may be a different coding sequence which coding sequence, as a result of the redundancy or degeneracy of the genetic code, encodes the same mature enzymes as the DNA of FIGS. 1–10 (SEQ ID NOS:23–32).

The polynucleotide which encodes for the mature enzyme of FIGS. 1–10 (SEQ ID NOS:33–42) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzymes having the deduced amino acid sequences of FIGS. 1–10 (SEQ ID NOS:33–42). The variant of the polynucleotide may be a naturally occurring allelic variant of the polynucleotide or a non-naturally occurring variant of the polynucleotide.

Thus, the present invention includes polynucleotides encoding the same mature enzymes as shown in FIGS. 1–10 (SEQ ID NOS:23–32) as well as variants of such polynucleotides which variants encode for a fragment, derivative or analog of the enzymes of FIGS. 1–10 (SEQ ID NOS:23–32). Such nucleotide variants include deletion variants, substitution variants and addition or insertion variants.

As hereinabove indicated, the polynucleotides may have a coding sequence which is a naturally occurring allelic variant of the coding sequences shown in FIGS. 1–10 (SEQ ID NOS:23–32). As known in the art, an allelic variant is an alternate form of a polynucleotide sequence which may have a substitution, deletion or addition of one or more nucleotides, which does not substantially alter the function of the encoded enzyme.

Fragments of the full length gene of the present invention may be used as hybridization probes for a cDNA or a genomic library to isolate the full length DNA and to isolate other DNAs which have a high sequence similarity to the gene or similar biological activity. Probes of this type preferably have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides having a sequence complementary to that of the gene of the present invention are used to screen a library of genomic DNA to determine which members of the library the probe hybridizes to.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other sources or to screen such sources for related sequences.

The present invention further relates to polynucleotides which hybridize to the hereinabove-described sequences if there is at least 70%, preferably at least 90%, and more preferably at least 95 % identity between the sequences. The present invention particularly relates to polynucleotides which hybridize under stringent conditions to the hereinabove-described polynucleotides. As herein used, the term "stringent conditions" means hybridization will occur only if there is at least 95 % and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of FIGS. 1–10 (SEQ ID NOS:23–32).

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotides of SEQ ID NOS:23–32, for example, for recovery of the polynucleotide or as a diagnostic probe or as a PCR primer.

Thus, the present invention is directed to polynucleotides having at least a 70% identity, preferably at least 90% identity and more preferably at least a 95 % identity to a polynucleotide which encodes the enzymes of SEQ ID NOS:33–42 as well as fragments thereof, which fragments have at least 15 bases, preferably at least 30 bases and most preferably at least 50 bases, which fragments are at least 90% identical, preferably at least 95 % identical and most preferably at least 97 % identical under stringent conditions to any portion of a polynucleotide of the present invention.

The present invention further relates to enzymes which have the deduced amino acid sequences of FIGS. 1–10 (SEQ ID NOS:23–32) as well as fragments, analogs and derivatives of such enzyme.

The terms "fragment," "derivative" and "analog" when referring to the enzymes of FIGS. 1–10 (SEQ ID NOS:33–42) mean enzymes which retain essentially the same biological function or activity as such enzymes. Thus, an analog includes a proprotein which can be activated by cleavage of the proprotein portion to produce an active mature enzyme.

The enzymes of the present invention may be a recombinant enzyme, a natural enzyme or a synthetic enzyme, preferably a recombinant enzyme.

The fragment, derivative or analog of the enzymes of FIGS. 1–10 (SEQ ID NOS:33–42) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The enzymes of the present invention include the enzymes of SEQ ID NOS:33–42 (in particular the mature enzyme) as well as enzymes which have at least 70% similarity (preferably at least 70% identity) to the enzymes of SEQ ID NOS:33–42 and more preferably at least 90% similarity (more preferably at least 90% identity) to the enzymes of SEQ ID NOS:33–42 and still more preferably at least 95% similarity (still more preferably at least 95 % identity) to the enzymes of SEQ ID NOS:33–42 and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme.

A variant, i.e. a "fragment", "analog" or "derivative" polypeptide, and reference polypeptide may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli,* Streptomyces, *Bacillus subtilis;* fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II KS, ptrc99a, pKK223-3, pDR540, pRIT2T (Pharmacia); Eukaryotic: pXT1, pSG5 (Stratagene) pSVK3, pBPV, pMSG, pSVL, SV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology,* (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual, Second Edition,* Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEMI (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

Esterases are a group of key enzymes in the metabolism of fats and are found in all organisms from microbes to mammals. In the hydrolysis reaction, an ester group is hydrolysed to an organic acid and an alcohol.

Esterases enantiomerically differentiate dicarboxylic diesters and diacetates of diols. Using the approach disclosed in a commonly assigned, copending provisional application Ser. No. 60/008,316, filed on Dec. 7, 1995 and entitled "Combinatorial Enzyme Development," the disclosure of which is incorporated herein by reference in its entirety, one could convert the enantiospecificity of the esterase. Further, the thermostable esterases are believed to have superior stability at higher temperatures and in organic solvents. Thus, they are better suited for use in rigorous production process which require robust catalysts.

There are a number of industrial and scientific applications for esterases, such as those of the present invention, including:

1) Esterases are useful in the dairy industry as ripening starters for cheeses, such as the Swiss-type cheeses;

2) Esterases are useful in the pulp and paper industry for lignin removal from cellulose pulps, for lignin solubilization by cleaving the ester linkages between aromatic acids and lignin and between lignin and hemicelluloses, and for disruption of cell wall structure when used in combination with xylanase and other xylan-degrading enzymes in biopulping and biobleaching of pulps;

3) Esterases are useful in the synthesis of carbohydrate derivatives, such as sugar derivatives;

4) Esterases are useful, when combined with xylanases and cellulases, in the conversion of lignocellulosic wastes to fermentable sugars for producing a variety of chemicals and fuels;

5) Esterases are useful as research reagents in studies on plant cell wall structure, particularly the nature of covalent bonds between lignin and carbohydrate polymers in the cell wall matrix;

6) Esterases are also useful as research reagents in studies on mechanisms related to disease resistance in plants and the process of organic matter decomposition; and 7) Esterases are useful in selection of plants bred for production of highly digestible animal feeds, particularly for ruminant animals.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, Nature, 256:495–497, 1975), the trioma technique, the human B-cell hybridoma technique (Kozbor et al., Immunology Today 4:72, 1983), and the EBV-hybridoma technique to produce human monoclonal antibodies (Cole et al., in Monoclonal Antibodies and Cancer Therapy, Alan R. Liss, Inc., pp. 77–96, 1985).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against an enzyme of the present invention may be used in screening for similar enzymes from other organisms and samples. Such screening techniques are known in the art, for example, one such screening assay is described in Sambrook et al., Molecular Cloning: A Laboratory Manual (2d Ed.), Cold Spring Harbor Laboratory, Section 12.21–12.28 (1989) which is hereby incorporated by reference in its entirety.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel et al., *Nucleic Acids Res.,* 8:4057 (1980). "Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated. "Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in Sambrook et al., Molecular Cloning: A Laboratory Manual (2d Ed.), Cold Spring Harbor Press (1989).

EXAMPLE 1

Bacterial Expression and Purification of Esterases

DNA encoding the enzymes of the present invention, SEQ ID NOS:33 through 42, were initially amplified from a pBluescript vector containing the DNA by the PCR technique using the primers noted herein. The amplified sequences were then inserted into the respective PQE vector listed beneath the primer sequences, and the enzyme was expressed according to the protocols set forth herein. The 5' and 3' primer sequences for the respective genes are as follows:

```
Straphylothermus marinus F1-12LC

5'   CCGAGAATTC ATTAAAGAGG AGAAATTAAC TATGTCTTTA AACAAGCACT CT
3'   CGGAAGATCT CTATCGTTTA GTGTATGATT T
vector: pQET Pyrodictium TAG11-17LC 5'   CCGAGAATTC ATTAAAGAGG AGAAATTAAC TATGAAACTC CTTGAGCCCA CA    EcoRI
3'   CGGAAGATCT CGCCGGTACA CCATCAGCCA C                           BglII
vector: pQET Archaeoglobus venificus SNP6-24LC 5'   CCGAGAATTC ATTAAAGAGG AGAAATTAAC TATGCCATAT GTTAGGAATG GT
3'   CGGAGGTACC TTAGAACTGT GCTGAAGAAA TAAATTCGTC CATTGCTCT
3'   CGGAGGTACC TTAGAACTGT GCTGAAGAAA TAAATTCGTC CATTGCTCTA TTA
vector: pQET Aquifex pyrophilus - 28LC 5'   CCGAGAATTC ATTAAAGAGG AGAAATTAAC TATGAGATTG AGGAAATTTG AAG
3'   CGGAGGTACC CTATTCAGAA AGTACCTCTA A
vector: pQET

M11TL - 29LC

5'   CCGAGAATTC ATTAAAGAGG AGAAATTAAC TATGTTTAAT ATCAATGTCT TT
3'   CGGAAGATCT TTAAGGATTT TCCCTGGGTA G
vector: pQET Thermococcus CL-2 - 30LC 5'   CCGAGAATTC ATTAAAGAGG AGAAATTAAC TATGGAGGTT TACAAGGCCA AA
3'   CGGAGGTACC TTATTGAGCC GAAGAGTACG A
vector: pQET Aquifex VF5 - 34LC 5'   CCGAGAATTC ATTAAAGAGG AGAAATTAAC TATGATTGGC AATTTGAAAT TGA   EcoRI
3'   CGGAGGTACC TTAAAGTGCT CTCATATCCC C                           KpnI
vector: pQET Teredinibacter 42L
```

-continued
```
5'  CCGAGAATTC ATTAAAGAGG AGAAATTAAC TATGCCAGCT AATGACTCAC CC
3'  CGGAAGATCT TCAACAGGCT CCAAATAATT TC  (without His-tag)
3'  CGGAAGATCT ACAGGCTCCA AATAATTTC  (with His-tag)
vector: pQE12
```

Archaeoglobus fulgidus VC16-16MC

```
5'  CCGAGAATTC ATTAAAGAGG AGAAATTAAC TATGCTTGAT ATGCCAATCG AC   EcoR1
3'  CGGAGGTACC CTAGTCGAAG ACAAGAAGAG C                          Kpn1
vector: pQET
```

Sulfolabus solfataricus P1-8LC

```
5'  CCGAGAATTC ATTAAAGAGG AGAAATTAAC TATGCCCCAG GATCCTAGAA TT   EcoR1
3'  CGGAGGTACC TTAAATTTTA TCATAAAATA C                          Kpn1
vector: pQET
```

The restriction enzyme sites indicated correspond to the restriction enzyme sites on the bacterial expression vector indicated for the respective gene (Qiagen, Inc. Chatsworth, Calif.). The pQE vector encodes antibiotic resistance (Amp$^r$), a bacterial origin of replication (ori), an IPTG-regulatable promoter operator (P/O), a ribosome binding site (RBS), a 6His tag and restriction enzyme sites.

The pQE vector was digested with the restriction enzymes indicated. The amplified sequences were ligated into the respective pQE vector and inserted in frame with the sequence encoding for the RBS. The ligation mixture was then used to transform the E. coli strain M15/pREP4 (Qiagen, Inc.) by electroporation. M15/pREP4 contains multiple copies of the plasmid pREP4, which expresses the lacI repressor and also confers kanamycin resistance (Kan$^r$). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lad repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

EXAMPLE 2

Isolation of a Selected Clone from the Deposited Genomic Clones

The two oligonucleotide primers corresponding to the gene of interest are used to amplify the gene from the deposited material. A polymerase chain reaction is carried out in 25 μl of reaction mixture with 0.1 μg of the DNA of the gene of interest. The reaction mixture is 1.5–5 mM MgCl$_2$, 0.01% (w/v) gelatin, 20 μM each of dATP, dCTP, dGTP, dTTP, 25 pmol of each primer and 1.25 Unit of Taq polymerase. Thirty cycles of PCR (denaturation at 94° C. for 1 min; annealing at 55° C. for 1 min; elongation at 72° C. for 1 min) are performed with the Perkin-Elmer Cetus 9600 thermal cycler. The amplified product is analyzed by agarose gel electrophoresis and the DNA band with expected molecular weight is excised and purified. The PCR product is verified to be the gene of interest by subcloning and sequencing the DNA product.

EXAMPLE 3

Production of the Expression Gene Bank

Colonies containing pBluescript plasmids with random inserts from the organisms M11TL, Thermococcus GU5L5, and Teredinibacter were obtained according to the method of Hay and Short, *Strategies*, 5:16, 1992.

EXAMPLE 4

Screening for Lipase/Esterase Activity

The resulting colonies were picked with sterile toothpicks and used to singly inoculate each of the wells of 96-well microtiter plates. The wells contained 250 μL of LB media with 100 μg/mL ampicillin, 80 μg/mL methicillin, and 10% v/v glycerol (LB Amp/Meth, glycerol). The cells were grown overnight at 37° C. without shaking. This constituted generation of the "Source GeneBank." Each well of the Source GeneBank thus contained a stock culture of E. coli cells, each of which contained a pBluescript with a unique DNA insert.

The plates of the Source GeneBank were used to multiply inoculate a single plate (the "Condensed Plate") containing in each well 200 μL of LB Amp/Meth, glycerol. This step was performed using the High Density Replicating Tool (HDRT) of the Beckman Biomek with a 1% bleach, water, isopropanol, air-dry sterilization cycle in between each inoculation. Each well of the Condensed Plate thus contained 10 to 12 different pBluescript clones from each of the source library plates. The Condensed Plate was grown for 16 hours at 37° C. and then used to inoculate two white 96-well Polyfiltronics microtiter daughter plates containing in each well 250 μL of LB Amp/Meth (no glycerol). The original condensed plate was put in storage −80° C. The two condensed daughter plates were incubated at 37° C. for 18 hours.

The short chain esterase '600 μM substrate stock solution' was prepared as follows: 25 mg of each of the following compounds was dissolved in the appropriate volume of DMSO to yield a 25.2 mM solution. The compounds used were 4-methylumbelliferyl proprionoate, 4-methylumbelliferyl butyrate, and 4-methylumbelliferyl heptanoate. Two hundred fifty microliters of each DMSO solution was added to ca 9 mL of 50 mM, pH 7.5 Hepes buffer which contained 0.6% of Triton X-100 and 0.6 mg per mL of dodecyl maltoside (Anatrace). The volume was taken to 10.5 mL with the above Hepes buffer to yield a slightly cloudy suspension.

The long chain '600 μM substrate stock solution' was prepared as follows: 25 mg of each of the following compounds was dissolved in DMSO to 25.2 mM as above. The compounds used were 4-methylumbelliferyl elaidate, 4-methylumbelliferyl palmitate, 4-methylumbelliferyl oleate, and 4-methylumbelliferyl stearate. All required brief warming in a 70° C. bath to achieve dissolution. Two hundred fifty microliters of each DMSO solution was added to the Hepes buffer and diluted to 10.5 mL as above. All seven umbelliferones were obtained from Sigma Chemical Co.

Fifty $\mu$L of the long chain esterase or short chain esterase '600 $\mu$M substrate stock solution' was added to each of the wells of a white condensed plate using the Biomek to yield a final concentration of substrate of about 100 $\mu$M.. The fluorescence values were recorded (excitation=326 nm, emission=450 nm) on a plate-reading fluorometer immediately after addition of the substrate. The plate was incubated at 70° C. for 60 minutes in the case of the long chain substrates, and 30 minutes at RT in the case of the short chain substrates. The fluorescence values were recorded again. The initial and final fluorescence values were compared to determine if an active clone was present.

EXAMPLE 5

Isolation and Purification of the Active Clone

To isolate the individual clone which carried the activity, the Source GeneBank plates were thawed and the individual wells used to singly inoculate a new plate containing LB Amp/Meth. As above, the plate was incubated at 37° C. to grow the cells, 50 $\mu$L of 600 $\mu$M substrate stock solution was added using the Biomek and the fluorescence was determined. Once the active well from the source plate was identified, cells from this active well were streaked on agar with LB/Amp/Meth and grown overnight at 37° C. to obtain single colonies. Eight single colonies were picked with a sterile toothpick and used to singly inoculate the wells of a 96-well microtiter plate. The wells contained 250 $\mu$L of LB Amp/Meth. The cells were grown overnight at 37° C. without shaking. A 200 $\mu$L aliquot was removed from each well and assayed with the appropriate long or short chain substrates as above. The most active clone was identified and the remaining 50 $\mu$L of culture was used to streak an agar plate with LB/Amp/Meth. Eight single colonies were picked, grown and assayed as above. The most active clone was used to inoculate 3 mL cultures of LB/Amp/Meth, which were grown overnight. The plasmid DNA was isolated from the cultures and utilized for sequencing.

Numerous modifications and variations of the present invention are possible in light of the above teachings and, therefore, within the scope of the appended claims, the invention may be practiced otherwise than as particularly described.

---

What is claimed is:

1. An isolated polynucleotide selected from the group consisting of:
   (a) a polynucleotide encoding an enzyme comprising an amino acid sequence as set forth in SEQ ID NO:33; and
   (b) a polynucleotide which is complementary to the polynucleotide of (a).

2. The polynucleotide of claim 1 wherein the polynucleotide is DNA.

3. The polynucleotide of claim 1 wherein the polynucleotide is RNA.

4. The polynucleotide of claim 1 which encodes an enzyme comprising amino acids 1 to 414 of SEQ ID NO:33.

5. An isolated polynucleotide encoding an enzyme having esterase activity selected from the group consisting of:

(a) SEQ ID NO:23;
   (b) SEQ ID NO:23, wherein T can also be U; and
   (c) fragments of (a) or (b) that are at least 15 bases in length.

6. An isolated polynucleotide as set forth in SEQ ID NO:23.

7. A vector comprising the DNA of claim 2.

8. A host cell comprising the vector of claim 7.

9. A process for producing a polypeptide comprising:
   (a) culturing a host cell of claim 8 under conditions that allow expression of the DNA; and
   (b) expressing from the host cell a polypeptide encoded by said DNA.

* * * * *

UNITED STATES PATENT AND TRADEMARK OFFICE
CERTIFICATE OF CORRECTION

PATENT NO. : 5,942,430  
DATED : August 24, 1999  
INVENTOR(S) : Dan E. Robertson et al.

It is certified that error appears in the above-identified patent and that said Letters Patent is hereby corrected as shown below:

<u>Column 63,</u>
Line 54, replace "414" with -- 184 --.

Signed and Sealed this

Thirteenth Day of January, 2004

JON W. DUDAS
*Acting Director of the United States Patent and Trademark Office*

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 52 NUCLEOTIDES
      (B) TYPE: NUCLEIC ACID
      (C) STRANDEDNESS: SINGLE
      (D) TOPOLOGY: LINEAR (ii) MOLECULE TYPE: cDNA (xi) SEQUENCE DESCRIPTION: SEQ ID NO:1:

CCGAGAATTC ATTAAAGAGG AGAAATTAAC TATGTCTTTA AACAAGCACT CT      52

(2) INFORMATION FOR SEQ ID NO:2:

(i) SEQUENCE CHARACTERISTICS:
      (A) LENGTH: 31 NUCLEOTIDES
      (B) TYPE: NUCLEIC ACID
      (C) STRANDEDNESS: SINGLE
      (D) TOPOLOGY: LINEAR (ii) MOLECULE TYPE: cDNA (xi) SEQUENCE DESCRIPTION: SEQ ID NO:2:

CGGAAGATCT CTATCGTTTA GTGTATGATT T      31

(2) INFORMATION FOR SEQ ID NO:3:

(i) SEQUENCE CHARACTERISTICS:
      (A) LENGTH: 52 NUCLEOTIDES
      (B) TYPE: NUCLEIC ACID
      (C) STRANDEDNESS: SINGLE
      (D) TOPOLOGY: LINEAR (ii) MOLECULE TYPE:  cDNA (xi) SEQUENCE DESCRIPTION:  SEQ ID NO:3:

CCGAGAATTC ATTAAAGAGG AGAAATTAAC TATGAAACTC CTTGAGCCCA CA            52

(2) INFORMATION FOR SEQ ID NO:4:

(i) SEQUENCE CHARACTERISTICS:
            (A) LENGTH:  31 NUCLEOTIDES
            (B) TYPE:  NUCLEIC ACID
            (C) STRANDEDNESS:  SINGLE
            (D) TOPOLOGY:  LINEAR (ii) MOLECULE TYPE:  cDNA (xi) SEQUENCE DESCRIPTION:  SEQ ID NO:4:

CGGAAGATCT CGCCGGTACA CCATCAGCCA C                                   31

(2) INFORMATION FOR SEQ ID NO:5:

(i) SEQUENCE CHARACTERISTICS:
            (A) LENGTH:  52 NUCLEOTIDES
            (B) TYPE:  NUCLEIC ACID
            (C) STRANDEDNESS:  SINGLE
            (D) TOPOLOGY:  LINEAR (ii) MOLECULE TYPE:  cDNA (xi) SEQUENCE DESCRIPTION:  SEQ ID NO:5:

CCGAGAATTC ATTAAAGAGG AGAAATTAAC TATGCCATAT GTTAGGAATG GT            52

(2) INFORMATION FOR SEQ ID NO:6:

(i) SEQUENCE CHARACTERISTICS:
            (A) LENGTH:  53 NUCLEOTIDES
            (B) TYPE:  NUCLEIC ACID
            (C) STRANDEDNESS:  SINGLE
            (D) TOPOLOGY:  LINEAR (ii) MOLECULE TYPE:  cDNA (xi) SEQUENCE DESCRIPTION:  SEQ ID NO:6:

CGGAGGTACC TTAGAACTGT GCTGAAGAAA TAAATTCGTC CATTGCTCTA TTA           53

(2) INFORMATION FOR SEQ ID NO:7:

(i) SEQUENCE CHARACTERISTICS:
            (A) LENGTH:  49 NUCLEOTIDES
            (B) TYPE:  NUCLEIC ACID
            (C) STRANDEDNESS:  SINGLE
            (D) TOPOLOGY:  LINEAR (ii) MOLECULE TYPE:  cDNA (xi) SEQUENCE DESCRIPTION:  SEQ ID NO:7:

CGGAGGTACC TTAGAACTGT GCTGAAGAAA TAAATTCGTC CATTGCTCT                49

(2) INFORMATION FOR SEQ ID NO:8:

(i) SEQUENCE CHARACTERISTICS:
            (A) LENGTH:  53 NUCLEOTIDES
            (B) TYPE:  NUCLEIC ACID
            (C) STRANDEDNESS:  SINGLE
            (D) TOPOLOGY:  LINEAR (ii) MOLECULE TYPE:  cDNA (xi) SEQUENCE DESCRIPTION:  SEQ ID NO:8:

CCGAGAATTC ATTAAAGAGG AGAAATTAAC TATGAGATTG AGGAAATTTG AAG           53

(2) INFORMATION FOR SEQ ID NO:9:

(i) SEQUENCE CHARACTERISTICS:
        (A) LENGTH: 31 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:9:

CGGAGGTACC CTATTCAGAA AGTACCTCTA A                              31

(2) INFORMATION FOR SEQ ID NO:10:

(i) SEQUENCE CHARACTERISTICS:
        (A) LENGTH: 52 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:10:

CCGAGAATTC ATTAAAGAGG AGAAATTAAC TATGTTTAAT ATCAATGTCT TT        52

(2) INFORMATION FOR SEQ ID NO:11:

(i) SEQUENCE CHARACTERISTICS:
        (A) LENGTH: 31 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:11:

CGGAAGATCT TTAAGGATTT TCCCTGGGTA G                              31

(2) INFORMATION FOR SEQ ID NO:12:

(i) SEQUENCE CHARACTERISTICS:
        (A) LENGTH: 52 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:12:

CCGAGAATTC ATTAAAGAGG AGAAATTAAC TATGGAGGTT TACAAGGCCA AA        52

(2) INFORMATION FOR SEQ ID NO:13:

(i) SEQUENCE CHARACTERISTICS:
        (A) LENGTH: 31 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:13:

CGGAGGTACC TTATTGAGCC GAAGAGTACG A                              31

(2) INFORMATION FOR SEQ ID NO:14:

(i) SEQUENCE CHARACTERISTICS:

(A) LENGTH: 53 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:14:

CCGAGAATTC ATTAAAGAGG AGAAATTAAC TATGATTGGC AATTTGAAAT TGA         53

(2) INFORMATION FOR SEQ ID NO:15:

(i) SEQUENCE CHARACTERISTICS:
        (A) LENGTH: 31 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:15:

CGGAGGTACC TTAAAGTGCT CTCATATCCC C                                31

(2) INFORMATION FOR SEQ ID NO:16:

(i) SEQUENCE CHARACTERISTICS:
        (A) LENGTH: 52 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:16:

CCGAGAATTC ATTAAAGAGG AGAAATTAAC TATGCCAGCT AATGACTCAC CC          52

(2) INFORMATION FOR SEQ ID NO:17:

(i) SEQUENCE CHARACTERISTICS:
        (A) LENGTH: 32 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:17:

CGGAAGATCT TCAACAGGCT CCAAATAATT TC                               32

(2) INFORMATION FOR SEQ ID NO:18:

(i) SEQUENCE CHARACTERISTICS:
        (A) LENGTH: 29 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:18:

CGGAAGATCT ACAGGCTCCA AATAATTTC                                   29

(2) INFORMATION FOR SEQ ID NO:19:

(i) SEQUENCE CHARACTERISTICS:
        (A) LENGTH: 52 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:19:

```
CCGAGAATTC ATTAAAGAGG AGAAATTAAC TATGCTTGAT ATGCCAATCG AC        52
```

(2) INFORMATION FOR SEQ ID NO:20:

(i) SEQUENCE CHARACTERISTICS:
        (A) LENGTH: 31 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:20:

```
CGGAGGTACC CTAGTCGAAC AGAAGAAGAG C                                31
```

(2) INFORMATION FOR SEQ ID NO:21:

(i) SEQUENCE CHARACTERISTICS:
        (A) LENGTH: 52 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:21:

```
CCGAGAATTC ATTAAAGAGG AGAAATTAAC TATGCCCCTA GATCCTAGAA TT        52
```

(2) INFORMATION FOR SEQ ID NO:22:

(i) SEQUENCE CHARACTERISTICS:
        (A) LENGTH: 31 NUCLEOTIDES
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:22:

```
CGGAGGTACC TTAAATTTTA TCATAAAATA C                                31
```

(2) INFORMATION FOR SEQ ID NO:23:

(i) SEQUENCE CHARACTERISTICS:
        (A) LENGTH: 555 NUCLEOTIDES
        (B) TYPE: NUCLEIC ACID
        (C) STRANDEDNESS: SINGLE
        (D) TOPOLOGY: LINEAR (ii) MOLECULE TYPE: GENOMIC DNA (xi) SEQUENCE DESCRIPTION: SEQ ID NO:23:

```
ATG TCT TTA AAC AAG CAC TCT TGG ATG GAT ATG ATA ATA TTT ATT CTC    48
Met Ser Leu Asn Lys His Ser Trp Met Asp Met Ile Ile Phe Ile Leu
 1               5                  10                  15

AGC TTT TCT TTC CCA TTA ACA ATG ATC GCA TTA GCT ATC TCT ATG TCG    96
Ser Phe Ser Phe Pro Leu Thr Met Ile Ala Leu Ala Ile Ser Met Ser
             20                  25                  30

TCA TGG TTT AAT ATA TGG AAT AAT GCA TTA AGC GAT CTA GGA CAT GCT   144
Ser Trp Phe Asn Ile Trp Asn Asn Ala Leu Ser Asp Leu Gly His Ala
         35                  40                  45

GTT AAA AGC AGT GTT GCT CCA ATA TTC AAT CTA GGT CTT GCA ATT GGT   192
Val Lys Ser Ser Val Ala Pro Ile Phe Asn Leu Gly Leu Ala Ile Gly
 50                  55                  60
```

```
GGG ATA CTA ATT GTT ATA GTT GGT TTA AGA AAT CTT TAT TCG TGG AGT        240
Gly Ile Leu Ile Val Ile Val Gly Leu Arg Asn Leu Tyr Ser Trp Ser
 65                  70                  75                  80

AGA GTT AAA GGA TCT TTA ATC ATA TCC ATG GGT GTA TTT CTT AAC TTA        288
Arg Val Lys Gly Ser Leu Ile Ile Ser Met Gly Val Phe Leu Asn Leu
                 85                  90                  95

ATA GGG GTT TTC GAC GAA GTA TAT GGT TGG ATA CAT TTC CTA GTC TCA        336
Ile Gly Val Phe Asp Glu Val Tyr Gly Trp Ile His Phe Leu Val Ser
            100                 105                 110

GTA TTG TTT TTC TTA TCA ATA ATA GCA TAT TTC ATA GCT ATA TCA ATA        384
Val Leu Phe Phe Leu Ser Ile Ile Ala Tyr Phe Ile Ala Ile Ser Ile
        115                 120                 125

CTT GAC AAA TCA TGG ATA GCT GTT CTA CTA ATA ATA GGT CAT ATT GCA        432
Leu Asp Lys Ser Trp Ile Ala Val Leu Leu Ile Ile Gly His Ile Ala
    130                 135                 140

ATG TGG TAT CTA CAC TTT GCT TCA GAG ATT CCG AGA GGT GCT GCT ATT        480
Met Trp Tyr Leu His Phe Ala Ser Glu Ile Pro Arg Gly Ala Ala Ile
145                 150                 155                 160

CCC GAG TTA TTA GCG GTA TTC TCG TTT TTA CCA TTC TAT ATA AGA CAG        528
Pro Glu Leu Leu Ala Val Phe Ser Phe Leu Pro Phe Tyr Ile Arg Asp
                165                 170                 175

TAT TTT AAA TCA TAC ACT AAA CGA TAG                                    555
Tyr Phe Lys Ser Tyr Thr Lys Arg
                180
```

(2) INFORMATION FOR SEQ ID NO:24:

(i) SEQUENCE CHARACTERISTICS:
        (A) LENGTH: 1041 NUCLEOTIDES
        (B) TYPE: NUCLEIC ACID
        (C) STRANDEDNESS: SINGLE
        (D) TOPOLOGY: LINEAR (ii) MOLECULE TYPE: GENOMIC DNA (xi) SEQUENCE DESCRIPTION: SEQ ID NO:24:

```
ATG AAA CTC CTT GAG CCC ACA AAT ACC TCC TAC ACG CTG TTA CAG GAT         48
Met Lys Leu Leu Glu Pro Thr Asn Thr Ser Tyr Thr Leu Leu Gln Asp
  1                   5                  10                  15

TTA GCA TTG CAT TTT GCA TTT TAC TGG TTT CTG GCC GTG TAT ACG TGG         96
Leu Ala Leu His Phe Ala Phe Tyr Trp Phe Leu Ala Val Tyr Thr Trp
                 20                  25                  30

TTA CCC GGT GTC CTA GTC CGG GGC GTA GCT GTG GAC ACA GGG GTG GCT        144
Leu Pro Gly Val Leu Val Arg Gly Val Ala Val Asp Thr Gly Val Ala
            35                  40                  45

CGG GTG CCT GGG CTC GGC CGG CGC GGT AAG AGG CTG CTC CTG GCC GCT        192
Arg Val Pro Gly Leu Gly Arg Arg Gly Lys Arg Leu Leu Leu Ala Ala
        50                  55                  60

GTG GCT GTC TTG GCG CTT GTT GTG TCC GTT GTT GTC CCG GCT TAT GTG        240
Val Ala Val Leu Ala Leu Val Val Ser Val Val Val Pro Ala Tyr Val
 65                  70                  75                  80

GCG TAT AGT AGT CTG CAC CCG GAG AGC TGT CGG CCC GTT GCG CCG GAG        288
Ala Tyr Ser Ser Leu His Pro Glu Ser Cys Arg Pro Val Ala Pro Glu
                 85                  90                  95

GGG CTC ACC TAC AAA GAG TTC AGC GTG ACC GCG GAG GAT GGC TTG GTG        336
Gly Leu Thr Tyr Lys Glu Phe Ser Val Thr Ala Glu Asp Gly Leu Val
            100                 105                 110

GTT CGG GGC TGG GTG CTG GGC CCC GGC GCT GGG GGC AAC CCG GTG TTC        384
Val Arg Gly Trp Cal Leu Gly Pro Gly Ala Gly Gly Asn Pro Val Phe
        115                 120                 125

GTT TTG ATG CAC GGG TAT ACT GGG TGC CGC TCG GCG CCC TAC ATG GCT        432
Val Leu Met His Gly Tyr Thr Gly Cys Arg Ser Ala Pro Tyr Met Ala
    130                 135                 140
```

```
GTG CTG GCC CGG GAG CTC GTG GAG TGG GGG TAC CCG GTG GTT GTG TTC        480
Val Leu Ala Arg Glu Leu Val Glu Trp Gly Tyr Pro Val Val Val Phe
145                 150                 155                 160

GAC TTC CGG GGC CAC GGG GAG AGC GGG GGC TCG ACG ACG ATT GGG CCC        528
Asp Phe Arg Gly His Gly Glu Ser Gly Gly Ser Thr Thr Ile Gly Pro
                165                 170                 175

CGG GAG GTG CTG GAT GCC CGG GCT GTG GTG GGC TAT GTC TCG GAG CGG        576
Arg Glu Val Leu Asp Ala Arg Ala Val Val Gly Tyr Val Ser Glu Arg
            180                 185                 190

TTC CCC GGC CGC CGG ATA ATA TTG GTG GGG TTC AGT ATG GGC GGC GCT        624
Phe Pro Gly Arg Arg Ile Ile Leu Val Gly Phe Ser Met Gly Gly Ala
        195                 200                 205

GTA GCG ATC GTG GAG GGT GCT GGG GAC CCG CGG GTC TAC GCG GTG GCT        672
Val Ala Ile Val Glu Gly Ala Gly Asp Pro Arg Val Tyr Ala Val Ala
    210                 215                 220

GCT GAT AGC CCG TAC TAT AGG CTC CGG GAC GTC ATA CCC CGG TGG CTG        720
Ala Asp Ser Pro Tyr Tyr Arg Leu Arg Asp Val Ile Pro Arg Trp Leu
225                 230                 235                 240

GAG TAC AAG ACG CCG CTG CCG GGC TGG GTG GGT GTG CTG GCC GGG TTC        768
Glu Tyr Lys Thr Pro Leu Pro Gly Trp Val Gly Val Leu Ala Gly Phe
                245                 250                 255

TAC GGG AGG CTG ATG GCG GGC GTT GAC CTC GGC TTC GGC CCC GCT GGG        816
Tyr Gly Arg Leu Met Ala Gly Val Asp Leu Gly Phe Gly Pro Ala Gly
            260                 265                 270

GTG GAG CGC GTG GAT AAG CCG TTG CTG GTG GTG TAT GGG CCC CGG GAC        864
Val Glu Arg Val Asp Lys Pro Leu Leu Val Val Tyr Gly Pro Arg Asp
        275                 280                 285

CCG CTG GTG ACG CGG GAC GAG GCG AGG AGC CTG GCG TCC CGT AGC CCG        912
Pro Leu Val Thr Arg Asp Glu Ala Arg Ser Leu Ala Ser Arg Ser Pro
    290                 295                 300

TGT GGC CGT CTC GTC GAG GTT CCT GGG GCT GGC CAC GTG GAG GCC GTG        960
Cys Gly Arg Leu Val Glu Val Pro Gly Ala Gly His Val Glu Ala Val
305                 310                 315                 320

GAT GTG CTC GGG CCG GGC CGC TAC GCA GAC ATG CTG ATA GAG CTG GCG       1008
Asp Val Leu Gly Pro Gly Arg Tyr Ala Asp Met Leu Ile Glu Leu Ala
                325                 330                 335

CAC GAG GAG TGC CCT CCG GGG GCC GGT GGC TGA                           1041
His Glu Glu Cys Pro Pro Gly Ala Gly Gly
            340                 345

(2) INFORMATION FOR SEQ ID NO:25:

(i) SEQUENCE CHARACTERISTICS:
          (A) LENGTH:  789 NUCLEOTIDES
          (B) TYPE:  NUCLEIC ACID
          (C) STRANDEDNESS:  SINGLE
          (D) TOPOLOGY:  LINEAR (ii) MOLECULE TYPE:  GENOMIC DNA (xi) SEQUENCE DESCRIPTION:  SEQ ID NO:25:

ATG CCA TAT GTT AGG AAT GGT GGT GTA AAT ATC TAT TAT GAA CTG GTG         48
Met Pro Tyr Val Arg Asn Gly Gly Val Asn Ile Tyr Tyr Glu Leu Val
  1               5                  10                  15

GAT GGA CCT GAG CCA CCA ATT GTC TTT GTT CAC GGA TGG ACA GCA AAT         96
Asp Gly Pro Glu Pro Pro Ile Val Phe Val His Gly Trp Thr Ala Asn
                 20                  25                  30

ATG AAT TTT TGG AAA GAG CAA AGA CGT TAT TTT GCA GGC AGG AAT ATG        144
Met Asn Phe Trp Lys Glu Gln Arg Arg Tyr Phe Ala Gly Arg Asn Met
             35                  40                  45

ATG TTG TTT GTC GAT AAC AGA GGT CAT GGC AGG TCC GAT AAG CCA CTT        192
Met Leu Phe Val Asp Asn Arg Gly His Gly Arg Ser Asp Lys Pro Leu
```

```
                50                    55                     60
GGA TAC GAT TTC TAC AGA TTT GAG AAC TTC ATT TCA GAT TTA GAT GCG       240
Gly Tyr Asp Phe Tyr Arg Phe Glu Asn Phe Ile Ser Asp Leu Asp Ala
 65                  70                  75                  80

GTT GTT AGG GAG ACT GGA GTG GAG AAA TTT GTT CTC GTC GGA CAT TCA       288
Val Val Arg Glu Thr Gly Val Glu Lys Phe Cal Leu Val Gly His Ser
                     85                  90                  95

TTC GGA ACA ATG ATC TCT ATG AAG TAC TGT TCG GAG TAT CGG AAT CGG       336
Phe Gly Thr Met Ile Ser Met Lys Tyr Cys Ser Glu Tyr Arg Asn Arg
                100                 105                 110

GTT CTT GCT CTA ATC CTC ATA GGT GGT GGG AGC AGA ATA AAG CTT CTA       384
Val Leu Ala Leu Ile Leu Ile Gly Gly Gly Ser Arg Ile Lys Leu Leu
            115                 120                 125

CAC AGA ATT GGA TAT CCT TTA GCA AAG ATT CTT GCA TCC ATT GCA TAC       432
His Arg Ile Gly Tyr Pro Leu Ala Lys Ile Leu Ala Ser Ile Ala Tyr
        130                 135                 140

AAG AAG TCT TCA AGA TTG GTC GCA GAT CTT TCC TTT GGC AAA AAT GCT       480
Lys Lys Ser Ser Arg Leu Val Ala Asp Leu Ser Phe Gly Lys Asn Ala
145                 150                 155                 160

GGT GAA CTT AAA GAG TGG GGA TGG AAA CAG GCA ATG GAT TAT ACA CCC       528
Gly Glu Leu Lys Glu Trp Gly Trp Lys Gln Ala Met Asp Tyr Thr Pro
                165                 170                 175

TCC TAC GTG GCA ATG GAC ACG TAC AGA ACT CTA ACG AAA GTG AAT CTT       576
Ser Tyr Val Ala Met Asp Thr Tyr Arg Thr Leu Thr Lys Val Asn Leu
            180                 185                 190

GAA AAT ATC TTG GAG AAA ATA GAC TGT CCA ACA CTG ATT ATC GTT GGA       624
Glu Asn Ile Leu Glu Lys Ile Asp Cys Pro Thr Leu Ile Ile Val Gly
        195                 200                 205

GAA GAG GAT GCA CTA TTG CCC GTT AGC AAA TCA GTT GAG CTG AGC AGG       672
Glu Glu Asp Ala Leu Leu Pro Val Ser Lys Ser Val Glu Leu Ser Arg
210                 215                 220

AGG ATA GAA AAC TCA AAG CTT GTG ATC ATC CCA AAC TCG GGG CAT TGC       720
Arg Ile Glu Asn Ser Lys Leu Val Ile Ile Pro Asn Ser Gly His Cys
225                 230                 235                 240

GTA ATG CTT GAG AGT CCA AGT GAG GTT AAT AGA GCA ATG GAC GAA TTC       768
Val Met Leu Glu Ser Pro Ser Glu Val Asn Arg Ala Met Asp Glu Phe
                245                 250                 255

ATT TCT TCA GCA CAG TTC TAA                                           789
Ile Ser Ser Ala Gln Phe
                260

(2) INFORMATION FOR SEQ ID NO:26:

(i) SEQUENCE CHARACTERISTICS:
        (A) LENGTH: 756 NUCLEOTIDES
        (B) TYPE: NUCLEIC ACID
        (C) STRANDEDNESS: SINGLE
        (D) TOPOLOGY: LINEAR (ii) MOLECULE TYPE: GENOMIC DNA (xi) SEQUENCE DESCRIPTION: SEQ ID NO:26:

TTG AGA TTG AGG AAA TTT GAA GAG ATA AAC CTC GTT CTT TCG GGA GGA        48
Leu Arg Leu Arg Lys Phe Glu Glu Ile Asn Leu Val Leu Ser Gly Gly
  1               5                  10                  15

GCT GCA AAG GGC ATA GCC CAC ATA GGT GTT TTG AAA GCT ATA AAC GAG        96
Ala Ala Lys Gly Ile Ala His Ile Gly Val Leu Lys Ala Ile Asn Glu
             20                  25                  30

CTC GGT ATA AGG GTG AGG GCT TTA AGC GGG GTG AGC GCC GGG GCA ATC       144
Leu Gly Ile Arg Val Arg Ala Leu Ser Gly Val Ser Ala Gly Ala Ile
         35                  40                  45

GTT TCG GTC TTT TAT GCC TCA GGC TAC TCC CCT GAA GGG ATG TTC AGC       192
```

```
Val Ser Val Phe Tyr Ala Ser Gly Tyr Ser Pro Glu Gly Met Phe Ser
     50              55              60

CTT CTG AAG AGG GTA AAC TGG CTG AAG CTG TTT AAG TTC AAG CCA CCT    240
Leu Leu Lys Arg Val Asn Trp Leu Lys Leu Phe Lys Phe Lye Pro Pro
65              70              75              80

CTG AAG GGA TTG ATA GGG TGG GAG AAG GCT ATA AGA TTC CTT GAG GAA    288
Leu Lys Gly Leu Ile Gly Trp Glu Lys Ala Ile Arg Phe Leu Glu Glu
                85              90              95

GTT CTC CCT TAC AGG AGA ATA GAA AAA CTT GAG ATA CCG ACG TAT ATA    336
Val Leu Pro Tyr Arg Arg Ile Glu Lys Leu GLu Ile Pro Thr Tyr Ile
            100             105             110

TGC GCG ACG GAT TTA TAC TCG GGA AGG GCT CTA TAC CTC TCG GAA GGG    384
Cys Ala Thr Asp Leu Tyr Ser Gly Arg Ala Leu Tyr Leu SEr Glu Gly
            115             120             125

AGT TTA ATC CCC GCA CTT CTC GGC AGC TGT GCA ATT CCC GGC ATA TTT    432
Ser Leu Ile Pro Ala Leu Leu Gly Ser Cys Ala Ile Pro Gly Ile Phe
        130             135             140

GAA CCC GTT GAG TAT AAG AAT TAC TTG CTC GTT GAC GGA GGT ATA GTT    480
Glu Pro Val Glu Tyr Lys Asn Tyr Leu Leu Val Asp Gly Gly Ile Val
145             150             155             160

AAC AAC CTT CCC GTT GAG CCC TTT CAG GAA AGC GGT ATT CCC ACC GTT    528
Asn Asn Leu Pro Val Glu Pro Phe Gln Glu Ser Gly Ile Pro Thr Val
            165             170             175

TGC GTT GAT GTC CTT CCC ATA GAG CCG GAA AAG GAT ATA AAG AAC ATT    576
Cys Val Asp Val Leu Pro Ile Glu Pro Glu Lys Asp Ile Lys Asn Ile
            180             185             190

CTT CAC ATC CTT TTG AGG AGC TTC TTT CTT GCG GTC CGC TCA AAC TCC    624
Leu His Ile Leu Leu Arg Ser Phe Phe Leu Ala Val Arg Ser Asn Ser
        195             200             205

GAA AAG AGA AAG GAG TTT TGT GAC CTC GTT ATA GTT CCT GAG CTT GAG    672
Glu Lys Arg Lys Glu Phe Cys Asp Leu Val Ile Val Pro Glu Leu Glu
210             215             220

GAG TTC ACA CCC CTT GAT GTT AGA AAA GCG GAC CAA ATA ATG GAG AGG    720
Glu Phe Thr Pro Leu Asp Val Arg Lys Ala Asp Gln Ile Met Glu Arg
225             230             235             240

GGA TAC ATA AAG GCC TTA GAG GTA CTT TCT GAA TAG                    756
Gly Tyr Ile Lys Ala Leu Glu Val Leu Ser Glu
            245             250

(2) INFORMATION FOR SEQ ID NO:27:

(i) SEQUENCE CHARACTERISTICS:
        (A) LENGTH:  894 NUCLEOTIDES
        (B) TYPE:  NUCLEIC ACID
        (C) STRANDEDNESS:  SINGLE
        (D) TOPOLOGY:  LINEAR (ii) MOLECULE TYPE:  GENOMIC DNA (xi) SEQUENCE DESCRIPTION:  SEQ ID NO:27:

ATG TTT AAT ATC AAT GTC TTT GTT AAT ATA TCT TGG CTG TAT TTT TCA    48
Met Phe Asn Ile Asn Val Phe Val Asn Ile Ser Trp Leu Tyr Phe Ser
1               5               10              15

GGG ATA GTT ATG AAG ACT GTG GAA GAG TAT GCG CTA CTT GAA ACA GGC    96
Gly Ile Val Met Lys Thr Val Glu Glu Tyr Ala Leu Leu Glu Thr Gly
            20              25              30

GTA AGA GTG TTT TAT CGG TGT GTA ATC CCG GAG AAA GCT TTT AAC ACT    144
Val Arg Val Phe Tyr Arg Cys Val Ile Pro Glu Lys Ala Phe Asn Thr
        35              40              45

TTG ATA ATA GGT TCA CAC GGA TTG GGG GCG CAC AGT GGA ATC TAC ATT    192
Leu Ile Ile Gly Ser His Gly Leu Gly Ala His Ser Gly Ile Tyr Ile
        50              55              60
```

```
AGT GTT GCT GAA GAA TTT GCT AGG CAC GGA TTT GGA TTC TGC ATG CAC        240
Ser Val Ala Glu Glu Phe Ala Arg His Gly Phe Gly Phe Cys Met His
 65                  70                  75                  80

GAT CAA AGG GGA CAT GGG AGA ACG GCA AGC GAT AGA GAA AGA GGG TAT        288
Asp Gln Arg Gly His Gly Arg Thr Ala Ser Asp Arg Glu Arg Gly Tyr
                     85                  90                  95

GTG GAG GGC TTT CAC AAC TTC ATA GAG GAT ATG AAG GCC TTC TCC GAT        336
Val Glu Gly Phe His Asn Phe Ile Glu Asp Met Lys Ala Phe Ser Asp
                100                 105                 110

TAT GCC AAG TGG CGC GTG GGA GGT GAC GAA ATA ATA TTG CTA GGA CAC        384
Tyr Ala Lys Trp Arg Val Gly Gly Asp Glu Ile Ile Leu Leu Gly His
            115                 120                 125

AGT ATG GGC GGG CTG ATA GCG CTC GGA ACA GTT GCA ACT TAT AAA GAA        432
Ser Met Gly Gly Leu Ile Ala Leu Gly Thr Val Ala Thr Tyr Lys Glu
130                 135                 140

ATC GCC AAG GGA GTT ATC GCG CTA GCC CCG GCC CTC CAA ATC CCC TTA        480
Ile Ala Lys Gly Val Ile Ala Leu Ala Pro Ala Leu Gln Ile Pro Leu
145                 150                 155                 160

ACC CCG GCT AGA AGA CTT GTT CTA AGC CTC GCG TCA AGG CTT GCC CCG        528
Thr Pro Ala Arg Arg Leu Val Leu Ser Leu Ala Ser Arg Leu Ala Pro
                165                 170                 175

CAT TCT AAG ATC ACC TTA CAA AGG AGA TTG CCG CAG AAA CCA GAG GGT        576
His Ser Lys Ile Thr Leu Gln Arg Arg Leu Pro Gln Lys Pro Glu Gly
            180                 185                 190

TTT CAA AGA GCA AAA GAT ATA GAA TAC AGT CTG AGT GAA ATA TCA GTC        624
Phe Gln Arg Ala Lys Asp Ile Glu Tyr Ser Leu Ser Glu Ile Ser Val
        195                 200                 205

AAG CTC GTG GAC GAA ATG ATT AAA GCA TCA TCT ATG TCT TGG ACC ATA        672
Lys Leu Val Asp Glu Met Ile Lys Ala Ser Ser Met Phe Trp Thr Ile
    210                 215                 220

GCA GGG GAA ATT AAT ACT CCC GTC CTG CTT ATT CAT GGG GAA AAA CAG        720
Ala Gly Glu Ile Asn Thr Pro Val Leu Leu Ile His Gly Glu Lys Asp
225                 230                 235                 240

AAT GTC ATA CCT CCG GAG GCG AGC AAA AAA GCC TAC CAA TTA ATA CCT        768
Asn Val Ile Pro Pro Glu Ala Ser Lys Lys Als Tyr Gln Leu Ile Pro
                245                 250                 255

TCA TTC CCT AAA GAG TTG AAA AAA TAC CCC GAT CTT GGA CAC AAC TTG        816
Ser Phe Pro Lys Glu Leu Lys Ile Tyr Pro Asp Leu Gly His Asn Leu
            260                 265                 270

TTT TTT GAA CCA GGC GCG GTG AAA ATC GTC ACA GAC ATT GTA GAG TGG        864
Phe Phe Glu Pro Gly Ala Val Lys Ile Val Thr Asp Ile Val Glu Trp
        275                 280                 285

GTT AAG AAT CTA CCC AGG GAA AAT CCT TAA                                894
Val Lys Asn Leu Pro Arg Glu Asn Pro
290                 295

(2) INFORMATION FOR SEQ ID NO:28:

(i) SEQUENCE CHARACTERISTICS:
        (A) LENGTH: 789 NUCLEOTIDES
        (B) TYPE: NUCLEIC ACID
        (C) STRANDEDNESS: SINGLE
        (D) TOPOLOGY: LINEAR (ii) MOLECULE TYPE: GENOMIC DNA (xi) SEQUENCE DESCRIPTION: SEQ ID NO:28:

ATG GAG GTT TAC AAG GCC AAA TTC GGC GAA GCA AAG CTC GGC TGG GTC         48
Met Glu Val Tyr Lys Ala Lys Phe Gly Glu Ala Lys Leu Gly Trp Val
  1                   5                  10                  15

GTT CTG GTT CAT GGC CTC GGC GAG CAC AGC GGA AGG TAT GGA AGA CTG         96
Val Leu Val His Gly Leu Gly Glu His Ser Gly Arg Tyr Gly Arg Leu
                 20                  25                  30
```

```
ATT AAG GAA CTC AAC TAT GCC GGC TTT GGA GTT TAC ACC TTC GAC TGG      144
Ile Lys Glu Leu Asn Tyr Ala Gly Phe Gly Val Tyr Thr Phe Asp Trp
         35                  40                  45

CCC GGC CAC GGG AAG AGC CCG GGC AAG AGA GGG CAC ACG AGC GTC GAG      192
Pro Gly His Gly Lys Ser Pro Gly Lys Arg Gly His Thr Ser Val Glu
     50                  55                  60

GAG GCG ATG GAA ATC ATC GAC TCG ATA ATC GAG GAG ATC AGG GAG AAG      240
Glu Ala Met Glu Ile Ile Asp Ser Ile Ile Glu Glu Ile Arg Glu Lys
 65                  70                  75                  80

CCC TTC CTC TTC GGC CAC AGC CTC GGT GGT CTA ACT GTC ATC AGG TAC      288
Pro Phe Leu Phe Gly His Ser Leu Gly Gly Leu Thr Val Ile Arg Tyr
                     85                  90                  95

GCT GAG ACG CGG CCC GAT AAA ATA CGG GGA TTA ATA GCT TCC TCG CCT      336
Ala Glu Thr Arg Pro Asp Lys Ile Arg Gly Leu Ile Ala Ser Ser Pro
                 100                 105                 110

GCC CTC GCC AAG AGC CCG GAA ACG CCG GGC TTC ATG GTG GCC CTC GCG      384
Ala Leu Ala Lys Ser Pro Glu Thr Pro Gly Phe Met Val Ala Leu Ala
             115                 120                 125

AAG TTC CTT GGA AAG ATC GCC CCG GGA GTT GTT CTC TCC AAC GGC ATA      432
Lys Phe Leu Gly Lys Ile Ala Pro Gly Val Val Leu Ser Asn Gly Ile
 130                 135                 140

AAG CCG GAA CTC CTC TCG AGG AAC AGG GAC GCC GTG AGG AGG TAC GTT      480
Lys Pro Glu Leu Leu Ser Arg Asn Arg Asp Ala Val Arg Arg Tyr Val
145                 150                 155                 160

GAA GAC CCA CTC GRC CAC GAC AGG ATT TCG GCC AAG CTG GGA AGG AGC      528
Glu Asp Pro Leu Val His Asp Arg Ile Ser Ala Lys Leu Gly Arg Ser
                 165                 170                 175

ATC TTC GTG AAC ATG GAG CTG GCC CAC AGG GAG GCG GAC AAG ATA AAA      576
Ile Phe Val Asn Met Glu Leu Ala His Arg Glu Ala Asp Lys Ile Lys
             180                 185                 190

GTC CCG ATC CTC CTT CTG ATC GGC ACT GGC GAT GTA ATA ACC CCG CCT      624
Val Pro Ile Leu Leu Leu Ile Gly Thr Gly Asp Val Ile Thr Pro Pro
         195                 200                 205

GAA GGC TCA CGC AGA CTC TTC GAG GAG CTG GCC GTC GAG AAC AAA ACC      672
Glu Gly Ser ARg Arg Leu Phe Glu Glu Leu Ala Val Glu Asn Lys Thr
 210                 215                 220

CTG AGG GAG TTC GAG GGG GCG TAC CAC GAG ATA TTT GAA GAC CCC GAG      720
Leu Arg Glu Phe Glu Gly Ala Tyr His Glu Ile Phe Glu Asp Pro Glu
225                 230                 235                 240

TGG GCC GAG GAG TTC CAC GAA ACA ATT GTT AAG TGG CTG GTT GAA AAA      768
Trp Ala Glu Glu Phe His Glu Thr Ile Val Lys Trp Leu Val Glu Lys
                 245                 250                 255

TCG TAC TCT TCG GCT CAA TAA                                          789
Ser Tyr Ser Ser Ala Gln
                 260
```

(2) INFORMATION FOR SEQ ID NO:29:

(i) SEQUENCE CHARACTERISTICS:
        (A) LENGTH: 750 NUCLEOTIDES
        (B) TYPE: NUCLEIC ACID
        (C) STRANDEDNESS: SINGLE
        (D) TOPOLOGY: LINEAR (ii) MOLECULE TYPE: GENOMIC DNA (xi) SEQUENCE DESCRIPTION: SEQ ID NO:29:

```
TTG ATT GGC AAT TTG AAA TTG AAG AGG TTT GAA GAG GTT AAC TTA GTT       48
Leu Ile Gly Asn Leu Lys Ley Lys Arg Phe Glu Glu Val Asn Leu Val
 1                   5                  10                  15

CTT TCG GGA GGG GCT GCC AAG GGT ATC GCC CAT ATA GGT GTT TTA AAA       96
Leu Ser Gly Gly Ala Ala Lys Gly Ile Ala His Ile Gly Val Leu Lys
```

```
                 20                  25                  30
GCT CTG GAA GAG CTC GGT ATA AAG GTA AAG AGG CTC AGC GGG GTA AGT      144
Ala Leu Glu Glu Leu Gly Ile Lys Val Lys Arg Leu Ser Gly Val Ser
             35                  40                  45

GCT GGA GCT ATC GTT TCC GTC TTT TAC GCT TCG GGC TAC ACT CCC GAC      192
Ala Gly Ala Ile Val Ser Val Phe Tyr Ala Ser Gly Tyr Thr Pro Asp
         50                  55                  60

GAG ATG TTA AAA CTC CTG AAA GAG GTA AAC TGG CTC AAA CTT TTT AAG      240
Glu Met Leu Lys Leu Leu Lys Glu Val Asn Trp Leu Lys Leu Phe Lys
 65                  70                  75                  80

TTC AAA ACA CCG AAA ATG GGC TTA ATG GGG TGG GAG AAG GCT GCA GAG      288
Phe Lys Thr Pro Lys Met Gly Leu Met Gly Trp Glu Lys Ala Ala Glu
             85                  90                  95

TTT TTG GAA AAA GAG CTC GGA GTT AAG AGG CTG GAA GAC CTG AAC ATA      336
Phe Leu Glu Lys Glu Leu Gly Val Lys Arg Leu Glu Asp Leu Asn Ile
            100                 105                 110

CCA ACC TAT CTT TGC TCG GCG GAT CTG TAC ACG GGA AAG GCT CTT TAC      384
Pro Thr Tyr Leu Cys Ser Ala Asp Ley Tyr Thr Gly Lys Ala Leu Tyr
            115                 120                 125

TTC GGC AGA GGT GAC TTA ATT CCC GTG CTT CTC GGA AGT TGT TCC ATA      432
Phe Gly Arg Gly Asp Leu Ile Pro Val Leu Leu Gly Ser Lys Ser Ile
        130                 135                 140

CCC GGG ATT TTT GAA CCA GTT GAG TAC GAG AAT TTT CTA CTT GTT GAC      480
Pro Gly Ile Phe Glu Pro Val Glu Tyr Glu Asn Phe Leu Leu Val Asp
145                 150                 155                 160

GGA GGT ATA GTG AAC AAC CTG CCC GTA GAA CCT TTG GAA AAG TTC AAA      528
Gly Gly Ile Val Asn Asn Leu Pro Val Glu Pro Leu Glu Lys Phe Lys
                165                 170                 175

GAA CCC ATA ATC GGG GTA GAT GTG CTT CCC ATA ACT CAA GAA AGA AAG      576
Glu Pro Ile Ile Gly Val Asp Val Leu Pro Ile Thr Gln Glu Arg Lys
            180                 185                 190

ATT AAA AAT ATA CTC CAC ATC CTT ATA AGG AGC TTC TTT CTG GCG GTT      624
Ile Lye Asn Ile Leu His Ile Leu Ile Arg Ser Phe Phe Leu Ala Val
            195                 200                 205

CGT TCC AAT TCG GAA AAG AGA AAG GAG TTC TGC AAC GTA GTT ATA GAA      672
Arg SEr Asn Ser Glu Lys Arg Lys Glu Phe Cys Asn Val Val Ile Glu
        210                 215                 220

CCT CCC CTT GAA GAG TTC TCT CCT CTG GAC GTA AAT AAG GCG GAC GAG      720
Pro Pro Leu Glu Glu Phe Ser Pro Leu Asp Val Asn Lys Ala Asp Glu
225                 230                 235                 240

ATA TTC TGC GGG GAT ATG AGA GCA CTT TAA                              750
Ile Phe Cys Gly Asp Met Arg Ala Leu
                245

(2) INFORMATION FOR SEQ ID NO:30:

(i) SEQUENCE CHARACTERISTICS:
        (A) LENGTH: 1017 NUCLEOTIDES
        (B) TYPE: NUCLEIC ACID
        (C) STRANDEDNESS: SINGLE
        (D) TOPOLOGY: LINEAR (ii) MOLECULE TYPE: GENOMIC DNA (xi) SEQUENCE DESCRIPTION: SEQ ID NO:30:

ATG CCA GCT AAT GAC TCA CCC ACG ATC GAC TTT AAT CCT CGC GGC ATT       48
Met Pro Ala Asn Asp Ser Pro Thr Ile Asp Phe Asn Pro Arg Gly Ile
  1               5                  10                  15

CTT CGC AAC GCT CAC GCA CAG GTT ATT TTA GCG ACT TCC GGC TTG CGC       96
Leu Arg Asn Ala His Ala Gln Val Ile Leu Ala Thr Ser Gly Leu Arg
             20                  25                  30

AAA GCG TTT TTG AAA CGC ACG CAC AAG AGC TAC CTC AGC ACT GCC CAA      144
```

```
                Lys Ala Phe Leu Lys Arg Thr His Lys Ser Tyr Leu Ser Thr Ala Gln
                             35                  40                  45

TGG CTG GAG CTC GAT GCC GGC AAC GGA GTT ACC TTG GCC GGA GAG CTT               192
Trp Leu Glu Leu Asp Ala Gly Asn Gly Val Thr Leu Ala Gly Glu Leu
         50                  55                  60

AAC ACA GCG CCT GCA ACT GCA TCC TCC TCC CAC CCG GCG CAC AAG AAC               240
Asn Thr Ala Pro Ala Thr Ala Ser Ser Ser His Pro Ala His Lys Asn
 65                  70                  75                  80

ACT CTG GTT ATT GTG CTG CAC GGC TGG GAA GGC TCC AGC CAG TCG GCC               288
Thr Leu Val Ile Val Leu His Gly Trp Glu Gly Ser Ser Gln Ser Ala
                         85                  90                  95

TAT GCG ACC TCC GCT GGC AGC ACG CTT TTC GAC AAT GGG TTC GAC ACT               336
Tyr Ala Thr Ser Ala Gly Ser Thr Leu Phe Asp Asn Gly Phe Asp Thr
                100                 105                 110

TTT CGC CTT AAT TTT CGC GAT CAC GGC GAC ACC TAC CAC TTA AAC CGC               384
Phe Arg Leu Asn Phe Arg Asp His Gly Asp Thr Tyr His Leu Asn Arg
            115                 120                 125

GGC ATA TTT AAC TCA TCG CTG ATT GAC GAA GTA GTG GGC GCA GTC AAA               432
Gly Ile Phe Asn Ser Ser Leu Ile Asp Glu Val Val Gly Ala Val Lys
130                 135                 140

GCC ATC CAG CAG CAA ACC GAC TAC GAC AAG TAT TGC CTG ATG GGG TTC               480
Ala Ile Gln Gln Gln Thr Asp Tyr Asp Lys Tyr Cys Leu Met Gly Phe
145                 150                 155                 160

TCA CTG GGT GGG AAC TTT GCC TTG CGC GTC GCG GTG CGG GAA CAG CAT               528
Ser Leu Gly Gly Asn Phe Ala Leu Arg Val Ala Val Arg Glu Gln His
                        165                 170                 175

CTC GCT AAA CCG CTA GCG GGC GTG CTC GCC GTA TGC CCG GTA CTC GAC               576
Leu Ala Lys Pro Leu Ala Gly Val Leu Ala Val Cys Pro Val Leu Asp
                180                 185                 190

CCC GCA CAC ACC ATG ATG GCC CTA AAC CGA GGT GCG TTT TTC TAC GGC               624
Pro Ala His Thr Met Met Ala Leu Asn Arg Gly Ala Phe Phe Tyr Gly
            195                 200                 205

CGC TAT TTT GCG CAT AAA TGG AAG CGC TCG TTA ACC GCA AAA CTT GCA               672
Arg Tyr Phe Ala His Lys Trp Lys Arg Ser Leu Thr Ala Lys Leu Ala
210                 215                 220                 225

GCT TTC CCA GAC TAC AAA TAC GGC AAA GAT TTA AAA TCG ATA CAC ACG               720
Ala Phe Pro Asp Tyr Lys Tyr Gly Lys Asp Leu Lys Ser Ile His Thr
                        230                 235                 240

CTT GAT GAG TTA AAC AAC TAT TTC ATT CCC CGC TAC ACC GGC TTC AAC               768
Leu Asp Glu Leu Asn Asn Tyr Phe Ile Pro Arg Tyr Thr Gly Phe Asn
                245                 250                 255

TCA GTC TCC GAA TAC TTC AAA AGT TAC ACG CTC ACC GGG CAG AAG CTC               816
Ser Val Ser Glu Tyr Phe Lys Ser Tyr Thr Leu Thr Gly Gln Lys Leu
            260                 265                 270

GCG TTT CTC AAC TGC CCC AGT TAC ATT CTG GCA GCT GGC GAC GAC CCA               864
Ala Phe Leu Asn Cys Pro Ser Tyr Ile Leu Ala Ala Gly Asp Asp Pro
        275                 280                 285

ATA ATT CCA GCA TCC GAC TTT CAG AAA ATA GCC AAG CCT GCG AAT CTG               912
Ile Ile Pro Ala Ser Asp Phe Gln Lys Ile Ala Lys Pro Ala Asn Leu
290                 295                 300                 305

CAC ATA ACA GTA ACG CAA CAA GGT TCT CAT TGC GCA TAC CTG GAA AAC               960
His Ile Thr Val Thr Gln Gln Gly Ser His Cys Ala Tyr Leu Glu Asn
                        310                 315                 320

CTG CAT AAA CCT AGT GCT GCC GAC AAA TAT GCG GTG AAA TTA TTT GGA              1008
Leu His Lys Pro Ser Ala Ala Asp Lys Tyr Ala Val Lys Leu Phe Gly
                325                 330                 335

GCC TGT TGA                                                                  1017
Ala Cys
```

(2) INFORMATION FOR SEQ ID NO:31:

(i) SEQUENCE CHARACTERISTICS:
    (A) LENGTH: 936 NUCLEOTIDES
    (B) TYPE: NUCLEIC ACID
    (C) STRANDEDNESS: SINGLE
    (D) TOPOLOGY: LINEAR (ii) MOLECULE TYPE: GENOMIC DNA (xi) SEQUENCE DESCRIPTION: SEQ ID NO:31:

```
ATG CTT GAT ATG CCA ATC GAC CCT GTT TAC TAC CAG CTT GCT GAG TAT        48
Met Leu Asp Met Pro Ile Asp Pro Val Tyr Tyr Gln Leu Ala Glu Tyr
 1               5                  10                  15

TTC GAC AGT CTG CCG AAG TTC GAC CAG TTT TCC TCG GCC AGA GAG TAC        96
Phe Asp Ser Leu Pro Lys Phe Asp GLn Phe Ser Ser Ala Arg Glu Tyr
                20                  25                  30

AGG GAG GCG ATA AAT CGA ATA TAC GAG GAG AGA AAC CGG CAG CTG AGC       144
Arg Glu Ala Ile Asn Arg Ile Tyr Glu Glu Arg Asn Arg Gln Leu Ser
            35                  40                  45

CAG CAT GAG AGG GTT GAA AGA GTT GAG GAC AGG ACG ATT AAG GGG AGG       192
Gln His Glu Arg Val Glu Arg Val Glu Asp Arg Thr Ile Lys Gly Arg
        50                  55                  60

AAC GGA GAC ATC AGA GTC AGA GTT TAC CAG CAG AAG CCC GAT TCC CCG       240
Asn Gly Asp Ile Arg Val Arg Val Tyr Gln Gln Lys Pro Asp Ser Pro
 65                 70                  75                  80

GGT CTG GTT TAC TAT CAC GGT GGT GGA TTT GTG ATT TGC AGC ATC GAG       288
Val Leu Val Tyr Tyr His Gly Gly Gly Phe Val Ile Cys Ser Ile Glu
                85                  90                  95

TCG CAC GAC GCC TTA TGC AGG AGA AYY GCG AGA CTT TCA AAC TCT ACC       336
Ser HIs Asp Ala Leu Cys Arg ARg Ile Ala Arg Leu Ser Asn Ser Thr
                100                 105                 110

GTA GTC TCC GTG GAT TAC AGG CTC GCT CCT GAG CAC AAG TTT CCC CCC       384
Val Val Ser Val Asp Tyr Arg Leu Ala Pro Glu His Lys Phe Pro Ala
            115                 120                 125

CCA GTT TAT CAT TGC TAC GAT GCG ACC AAG TGG GTT GCT GAG AAC CGG       432
Ala Val Tyr Asp Cys Tyr Aso Ala Thr Lys Trp Val Ala Glu Asn Ala
        130                 135                 140

GAG GAG CTG AGG ATT GAC CCG TCA AAA ATC TTC GTT GGG GGG GAC AGT       480
Glu Glu Leu Arg Ile Asp Pro Ser Lys Ile Phe Val Gly Gly Asp Ser
145                 150                 155                 160

GCG GGA CGG AAT CTT GCC CCG GCG CTT TCA ATA ATG GCG AGA GAC AGC       528
Ala Gly Gly Asn Leu Ala Ala Ala Val Ser Ile Met Ala Arg Asp Ser
                165                 170                 175

GGA GAA GAT TTC ATA AAG CAT CAA ATT CTA ACT TAC CCC GTT GTG AAC       576
Gly Glu Asp Phe Ile Lys His Gln Ile Leu Ile Tyr Pro Val Val Asn
            180                 185                 190

TTT GTA GCC CCC ACA CCA TCG CTT CTG GAG TTT GGA GAG GGG CTG TGG       624
Phe Val Ala Pro Thr Pro Ser Leu Leu Glu Phe GLy Glu Gly Leu Trp
        195                 200                 205

ATT CTC GAC CAG AAG ATA ATG AGT TGG TTC TCG GAG CAG TAC TTC TCC       672
Ile Leu Asp Gln Lys Ile Met Ser Trp Phe Ser Glu Gln Tyr Phe Ser
    210                 215                 230

AGA GAG GAA GAT AAG TTC AAG CCC CTC GCC TCC GTA ATC TTT GCG GAC       720
Arg Glu Glu Aso Lys Phe Asn Pro Leu Ala Ser Val Ile Phe Ala Asp
235                 240                 245                 250

CTT GAG AAC CTA CCT CCT GCG CTG ATC ATA ACC GCC GAA TAC GAC CCG       768
Leu Glu Asn Leu Pro Pro Ala Leu Ile Ile Thr Ala Glu Tyr Asp Pro
                255                 260                 265

CTG AGA GAT GAA GGA GAA GTT TTC GGG CAG ATG CTG AGA AGA GCC GGT       816
Leu Arg Asp Glu Gly Glu Val Phe Gly Gln Met Leu Arg Arg Ala Gly
            270                 275                 280

GTT GAG GCG AGC ATC GTC AGA TAC AGA GGC GTG CTT CAC GGA TTC ATC       864
```

```
Val Glu Ala Ser Ile Val Arg Tyr Arg Gly Val Leu His Gly Phe Ile
    285                 290                 295

AAT TAC TAT CCC GTG CTG AAG GCT GCG AGG GAT GCG ATA AAC CAG ATT   912
Asn Tyr Tyr Pro Val Leu Lys Ala Ala Arg Asp Ala Ile Asn Gln Ile
300                 305                 310

GCC GCT CTT CTT GTG TTC GAC TAG                                   936
Ala Ala Leu leu Val Phe Asp
315                 320

(2) INFORMATION FOR SEQ ID NO:32:

(i) SEQUENCE CHARACTERISTICS:
        (A) LENGTH: 918 NUCLEOTIDES
        (B) TYPE: NUCLEIC ACID
        (C) STRANDEDNESS: SINGLE
        (D) TOPOLOGY: LINEAR (ii) MOLECULE TYPE: GENOMIC DNA (xi) SEQUENCE DESCRIPTION: SEQ ID NO:32:

ATG CCC CTA GAT CCT AGA ATT AAA AAG TTA CTA GAA TCA GCT CTT ACT   48
Met Pro Leu Asp Pro Arg Ile Lys Lys Leu Leu Glu Ser Ala Leu Thr
            5                  10                  15

ATA CCA ATT GGT AAA GCC CCA GTA GAA GAG GTA AGA AAG ATA TTT AGG   96
Ile Pro Ile Gly Lys Ala Pro Val Glu Glu Val Arg Lys Ile Phe Arg
            20                  25                  30

CAA TTA GCG TCG GCA GCT CCC AAA GTC GAA GTT GGA AAA GTA GAA GAT   144
Gln Leu Ala Ser Ala Ala Pro Lys Val Glu Val Gly Lys Val Glu Asp
            35                  40                  45

ATA AAA ATA CCA GGC AGT GAA ACC GTT ATA AAC GCT AGA GTG TAT TTT   192
Ile Lys Ile Pro Gly Ser Glu Thr Val Ile Asn Ala Arg Val Tyr Phe
    50                  55                  60

CCG AAG AGT AGC GGT CCT TAT GGT GTT CTA GTG TAT CTT CAT GGA GGC   240
Pro Lys Ser Ser Gly Pro Tyr Gly Val Leu Val Tyr Leu His Gly Gly
65                  70                  75                  80

GGT TTT GTA ATA GGC GAT GTG GAA TCT TAT GAC CCA TTA TGT AGA GCA   288
Gly Phe Val Ile Gly Asp Val Glu Ser Tyr Asp Pro Leu Cys Arg Ala
                85                  90                  95

ATT ACA AAT GCG TGC AAT TGC GTT GTA GTA TCA GTG GAC TAT AGG TTA   336
Ile Thr Asn Ala Cys Asn Cys Val Val Val Ser Val Asp Tyr Arg Leu
            100                 105                 110

GCT CCA GAA TAC AAG TTT CCT TCT GCA GTT ATC GAT TCA TTT GAC GCT   384
Ala Pro Glu Tyr Lys Phe Pro Ser Ala Val Ile Asp Ser Phe Asp Ala
            115                 120                 125

ACT AAT TGG GTT TAT AAC AAT TTA GAT AAA TTT GAT GGA AAG ATG GGA   432
Thr Asn Trp Val Tyr Asn Asn Leu Asp Lys Phe Asp Gly Lys Met Gly
            130                 135                 140

GTT GCG ATT GCG GGA GAT AGT GCT GGA GGA AAT TTG GCA GCG GTT GTA   480
Val Ala Ile Ala Gly Asp Ser Ale Gly Gly Asn Leu Ala Ala Val Val
145                 150                 155                 160

GCT CTT CTT TCA AAG GGT AAA ATT AAT TTG AAG TAT CAA ATA CTG GTT   528
Ala Leu Leu Ser Lys Gly Lys Ile Asn Leu Lys Tyr Gln Ile Leu Val
                165                 170                 175

TAC CCA GCG GTA AGT TTA GAT AAC GTT TCA AGA TCC ATG ATA GAG TAC   576
Tyr Pro Ala Val Ser Leu Asp Asn Val Ser Arg Ser Met Ile Glu Tyr
            180                 185                 190

TCT GAT GGG TTC TTC CTT ACC AGA GAG CAT ATA GAG TGG TTC GGT TCT   624
Ser Asp Gly Phe Phe Leu Thr Arg Glu His Ile Glu Trp Phe Gly Ser
            195                 200                 205

CAA TAC TTA CGA AGC CCT GCA GAT TTG CTA GAC TTT AGG TTC TCT CCA   672
Gln Tyr Leu Arg Ser Pro Ala Asp Leu Leu Asp Phe Arg Phe Ser Pro
            210                 215                 220
```

```
ATT CTG GCG CAA GAT TTC AAC GGA TTA CCT CCA GCC TTG ATA ATA ACA        720
Ile Leu Ala Gln Asp Phe Asn Gly Leu Pro Pro Ala Leu Ile Ile Thr
225                 230                 235                 240

GCA GAA TAC GAT CCA CTA AGG GAT CAA GGA GAA GCG TAT GCA AAT AAA        768
Ala Glu Tyr Asp Pro Leu Arg Asp Gln Gly Glu Ala Tyr Ala Asn Lys
            245                 250                 255

CTA CTA CAA GCT GGA GTC TCA GTT ACT AGT GTG AGA TTT AAC AAC GTT        816
Leu Leu Gln Ala Gly Val Ser Val Thr Ser Val Arg Phe Asn Asn Val
        260                 265                 270

ATA CAC GGA TTC CTC TCA TTC TTT CCG TTG ATG GAG CAA GGA AGA GAT        864
Ile His Gly Phe Leu Ser Phe Phe Pro Leu Met Glu Gln Gly Arg Asp
    275                 280                 285

GCT ATA GGT CTG ATA GGG TCT GTG TTA AGA CGA GTA TTT TAT GAT AAA        912
Ala Ile Gly Leu Ile Gly Ser Val Leu Arg Arg Val Phe Tyr Asp Lys
290                 295                 300

ATT TAA                                                                918
Ile
305

(2) INFORMATION FOR SEQ ID NO:33:

(i) SEQUENCE CHARACTERISTICS:
        (A) LENGTH: 184 AMINO ACIDS
        (B) TYPE: AMINO ACID
        (D) TOPOLOGY: LINEAR (ii) MOLECULE TYPE: PROTEIN (xi) SEQUENCE DESCRIPTION: SEQ ID NO:33:

Met Ser Leu Asn Lys His Ser Trp Met Asp Met Ile Ile Phe Ile Leu
1               5                   10                  15

Ser Phe Ser Phe Pro Leu Thr Met Ile Ala Leu Ala Ile Ser Met Ser
            20                  25                  30

Ser Trp Phe Asn Ile Trp Asn Asn Ala Leu Ser Asp Leu Gly His Ala
        35                  40                  45

Val Lys Ser Ser Val Ala Pro Ile Phe Asn Leu Gly Leu Ala Ile Gly
    50                  55                  60

Gly Ile Leu Ile Val Ile Val Gly Leu Arg Asn Leu Tyr Ser Trp Ser
65                  70                  75                  80

Arg Val Lys Gly Ser Leu Ile Ile Ser Met Gly Val Phe Leu Asn Leu
                85                  90                  95

Ile Gly Val Phe Asp Glu Val Tyr Gly Trp Ile His Phe Leu Val Ser
            100                 105                 110

Val Leu Phe Phe Leu Ser Ile Ile Ala Tyr Phe Ile Ala Ile Ser Ile
        115                 120                 125

Leu Asp Lys Ser Trp Ile Ala Val Leu Leu Ile Ile Gly His Ile Ala
    130                 135                 140

Met Trp Tyr Leu His Phe Ala Ser Glu Ile Pro Arg Gly Ala Ala Ile
145                 150                 155                 160

Pro Glu Leu Leu Ala Val Phe Ser Phe Leu Pro Phe Tyr Ile Arg Asp
                165                 170                 175

Tyr Phe Lys Ser Tyr Thr Lys Arg
            180

(2) INFORMATION FOR SEQ ID NO:34:

(i) SEQUENCE CHARACTERISTICS:
        (A) LENGTH: 346 AMINO ACIDS
        (B) TYPE: AMINO ACID
        (D) TOPOLOGY: LINEAR
```

(ii) MOLECULE TYPE: PROTEIN (xi) SEQUENCE DESCRIPTION: SEQ ID NO:34:

```
Met Lys Leu Leu Glu Pro Thr Asn Thr Ser Tyr Thr Leu Leu Gln Asp
 1               5                  10                  15

Leu Ala Leu His Phe Ala Phe Tyr Trp Phe Leu Ala Val TYr Thr Trp
                20                  25                  30

Leu Pro Gly Val Leu Val Arg Gly Val Ala Val Asp Thr Gly Val Ala
                35                  40                  45

Arg Val Pro Gly Leu Gly Arg Arg Gly Lys Arg Leu Leu Leu Ala Ala
            50                  55                  60

Val Ala Val Leu Ala Leu Val Val Ser Val Val Pro Ala Tyr Val
65                  70                  75                  80

Ala Tyr Ser Ser Leu His Pro Glu Ser Cys Arg Pro Val Ala Pro Glu
                    85                  90                  95

Gly Leu Thr Tyr Lys Glu Phe Ser Val Thr Ala Glu Asp Gly Leu Val
                100                 105                 110

Val Arg Gly Trp Val Leu Gly Pro Gly Ala Gly Gly Asn Pro Val Phe
                115                 120                 125

Val Leu Met His Gly Tyr Thr Gly Cys Arg Ser Ala Pro Tyr Met Ala
            130                 135                 140

Val Leu Ala Arg Glu Leu Val Glu Trp Gly Tyr Pro Val Val Val Phe
145                 150                 155                 160

Asp Phe Arg Gly His Gly Glu Ser Gly Gly Ser Thr Thr Ile Gly Pro
                    165                 170                 175

Arg Glu Val Leu Asp Ala Arg Ala Val Val Gly Tyr Val Ser Glu Arg
                180                 185                 190

Phe Pro Gly Arg Arg Ile Ile Leu Val Gly Phe Ser Met Gly Gly Ala
                195                 200                 205

Val Ala Ile Val Glu Gly Ala Gly Asp Pro Arg Val Tyr Ala Val Ala
            210                 215                 220

Ala Asp Ser Pro Tyr Tyr Arg Leu Arg Asp Val Ile Pro Arg Trp Leu
225                 230                 235                 240

Glu Tyr Lys Thr Pro Leu Pro Gly Trp Val Gly Val Leu Ala Gly Phe
                    245                 250                 255

Tyr Gly Arg Leu Met Ala Gly Val Asp Leu Gly Phe Gly Pro Ala Gly
                260                 265                 270

Val Gly Arg Val Asp Lys Pro Leu Leu Val Val Tyr Gly Pro Arg Asp
            275                 280                 285

Pro Leu Val Thr Arg Asp Glu Ala Arg Ser Leu Ala Ser Arg Ser Pro
290                 295                 300

Cys Gly Arg Leu Val Glu Val Pro Gly Ala Gly His Val Glu Ala Val
305                 310                 315                 320

Asp Val Leu Gly Pro Gly Arg Tyr Ala Asp Met Leu Ile Glu Leu Ala
                325                 330                 335

His Glu Glu Cys Pro Pro Gly Ala Gly Gly
                340                 345
```

(2) INFORMATION FOR SEQ ID NO:35:

(i) SEQUENCE CHARACTERISTICS:
      (A) LENGTH: 262 AMINO ACIDS
      (B) TYPE: AMINO ACID
      (D) TOPOLOGY: LINEAR (ii) MOLECULE TYPE: PROTEIN 5,942,430

51

52

-continued (xi) SEQUENCE DESCRIPTION: SEQ ID NO:35:

```
Met Pro Tyr Val Arg Asn Gly Val Asn Ile Tyr Tyr Glu Leu Val
  1               5                  10                  15

Asp Gly Pro Glu Pro Pro Ile Val Phe Val His Gly Trp Thr Ala Asn
              20                  25                  30

Met Asn Phe Trp Lys Glu Gln Arg Arg Tyr Phe Ala Gly Arg Asn Met
          35                  40                  45

Met Leu Phe Val Asp Asn Arg Gly His Gly Arg Ser Asp Lys Pro Leu
     50                  55                  60

Gly Tyr Asp Phe Tyr Arg Phe Glu Asn Phe Ile Ser Asp Leu Asp Ala
 65                  70                  75                  80

Val Val Arg Glu Thr Gly Val Glu Lys Phe Val Leu Val Gly His Ser
                 85                  90                  95

Phe Gly Thr Met Ile Ser Met Lys Tyr Cys Ser Glu Tyr Arg Asn Arg
                100                 105                 110

Val Leu Ala Leu Ile Leu Ile Gly Gly Ser Arg Ile Lys Leu Leu
             115                 120                 125

His Arg Ile Gly Tyr Pro Leu Ala Lys Ile Leu Ala Ser Ile Ala Tyr
            130                 135                 140

Lys Lys Ser Ser Arg Leu Val Ala Asp Leu Ser Phe Gly Lys Asn Ala
145                 150                 155                 160

Gly Glu Leu Lys Glu Trp Gly Trp Lys Gln Ala Met Asp Tyr Thr Pro
                165                 170                 175

Ser Tyr Val Ala Met Tyr Thr Tyr Arg Thr Leu Thr Lys Val Asn Leu
            180                 185                 190

Glu Asn Ile Leu Glu Lys Ile Asp Cys Pro Thr Leu Ile Ile Val Gly
        195                 200                 205

Glu Glu Asp Ala Leu Leu Pro Val Ser Lys Ser Val Glu Leu Ser Arg
    210                 215                 220

Arg Ile Glu Asn Ser Lys Leu Val Ile Ile Pro Asn Ser Gly His Cys
225                 230                 235                 240

Val Met Leu Glu Ser Pro Ser Val Asn Arg Ala Met Asp Glu Phe
                245                 250                 255

Ile Ser Ser Ala Gln Phe
260
```

(2) INFORMATION FOR SEQ ID NO:36:

(i) SEQUENCE CHARACTERISTICS:
        (A) LENGTH: 251 AMINO ACIDS
        (B) TYPE: AMINO ACID
        (D) TOPOLOGY: LINEAR (ii) MOLECULE TYPE: PROTEIN (xi) SEQUENCE DESCRIPTION: SEQ ID NO:36:

```
Leu Arg Leu Arg Lys Phe Glu Glu Ile Asn Leu Val Leu Ser Gly Gly
  1               5                  10                  15

Ala Ala Lys Gly Ile Ala His Ile Gly Val Leu Lys Ala Ile Asn Glu
              20                  25                  30

Leu Glu Ile Arg Val Arg Ala Leu Ser Gly Val Ser Ala Gly Ala Ile
          35                  40                  45

Val Ser Val Phe Tyr Ala Ser Gly Tyr Ser Pro Glu Gly Met Phe Ser
     50                  55                  60

Leu Leu Lys Arg Val Asn Trp Leu Lys Leu Phe Lys Phe Lys Pro Pro
 65                  70                  75                  80
```

```
Leu Lys Gly Leu Ile Gly Trp Glu Lys Ala Ile Arg Phe Leu Glu Glu
                85                  90                  95

Val Leu Pro Tyr Arg Arg Ile Glu Lys Leu GLu Ile Pro Thr Tyr Ile
            100                 105                 110

Cys Ala Thr Asp Leu Tyr Ser Gly Arg Ala Leu Tyr Leu SEr Glu Gly
            115                 120                 125

Ser Leu Ile Pro Ala Leu Leu Gly Ser Cys Ala Ile Pro Gly Ile Phe
        130                 135                 140

Glu Pro Val Glu Tyr Lys Asn Tyr Leu Leu Val Asp Gly Gly Ile Val
145                 150                 155                 160

Asn Asn Leu Pro Val Glu Pro Phe Gln Glu Ser Gly Ile Pro Thr Val
                165                 170                 175

Cys Val Asp Val Leu Pro Ile Glu Pro Glu Lys Asp Ile Lys Asn Ile
            180                 185                 190

Leu His Ile Leu Leu Arg Ser Phe Phe Leu Ala Val Arg Ser Asn Ser
            195                 200                 205

Glu Lys Arg Lys Glu Phe Cys Asp Leu Val Ile Val Pro Glu Leu Glu
            210                 215                 220

Glu Phe Thr Pro Leu Asp Val Arg Lys Ala Asp Gln Ile Met Glu Arg
225                 230                 235                 240

Gly Tyr Ile Lys Ala Leu Glu Val Leu Ser Glu
                245                 250

(2) INFORMATION FOR SEQ ID NO:37:

(i) SEQUENCE CHARACTERISTICS:
        (A) LENGTH: 297 AMINO ACIDS
        (B) TYPE: AMINO ACID
        (D) TOPOLOGY: LINEAR (ii) MOLECULE TYPE: PROTEIN (xi) SEQUENCE DESCRIPTION: SEQ ID NO:37:

Met Phe Asn Ile Asn Val Phe Val Asn Ile Ser Trp Leu Tyr Phe Ser
 1               5                  10                  15

Gly Ile Val Met Lys Thr Val Glu Glu Tyr Ala Leu Leu Glu Thr Gly
                20                  25                  30

Val Arg Val Phe Tyr Arg Cys Val Ile Pro Glu Lys Ala Phe Asn Thr
            35                  40                  45

Leu Ile Ile Gly Ser His Gly Leu Gly Ala His Ser Gly Ile Tyr Ile
        50                  55                  60

Ser Val Ala Glu Glu Phe Ala Arg His Gly Phe Gly Phe Cys Met His
65                  70                  75                  80

Asp Gln Arg Gly His Gly Arg Thr Ala Ser Asp Arg Glu Arg Gly Tyr
                85                  90                  95

Val Glu Gly Phe His Asn Phe Ile Glu Asp Met Lys Ala Phe Ser Asp
            100                 105                 110

Tyr Ala Lys Trp Arg Val Gly Gly Asp Glu Ile Ile Leu Leu Gly His
            115                 120                 125

Ser Met Gly Gly Leu Ile Ala Leu Leu Thr Val Ala Thr Tyr Lys Glu
        130                 135                 140

Ile Ala Lys Gly Val Ile Ala Leu Ala Pro Ala Leu Gln Ile Pro Leu
145                 150                 155                 160

Thr Pro Ala Arg Arg Leu Val Leu Ser Leu Ala Ser Arg Leu Ala Pro
                165                 170                 175

His Ser Lys Ile Thr Leu Gln Arg Arg Leu Pro Gln Lys Pro Glu Gly
            180                 185                 190
```

```
Phe Gln Arg Ala Lys Asp Ile Glu Tyr Ser Leu Ser Glu Ile Ser Val
            195                 200                 205

Lys Leu Val Asp Glu Met Ile Lys Ala Ser Ser Met Phe Trp Thr Ile
210                 215                 220

Ala Gly Glu Ile Asn Thr Pro Val Leu Leu Ile His Gly Glu Lys Asp
225                 230                 235                 240

Asn Val Ile Pro Pro Glu Ala Ser Lys Lys Ala Tyr Gln Leu Ile Pro
            245                 250                 255

Ser Phe Pro Lys Glu Leu Lys Ile Tyr Pro Asp Leu Gly His Asn Leu
            260                 265                 270

Phe Phe Glu Pro Gly Ala Val Lys Ile Val Thr Asp Ile Val Glu Trp
            275                 280                 285

Val Lys Asn Leu Pro Arg Glu Asn Pro
290                 295

(2) INFORMATION FOR SEQ ID NO:38:

(i) SEQUENCE CHARACTERISTICS:
        (A) LENGTH:  262 AMINO ACIDS
        (B) TYPE:  AMINO ACID
        (D) TOPOLOGY:  LINEAR (ii) MOLECULE TYPE:  PROTEIN (xi) SEQUENCE DESCRIPTION:  SEQ ID NO:38:

Met Glu Val Tyr Lys Ala Lys Phe Gly Glu Ala Lys Leu Gly Trp Val
1                   5                  10                  15

Val Leu Val His Gly Leu Gly Glu His Ser Gly Arg Tyr Gly Arg Leu
            20                  25                  30

Ile Lys Glu Leu Asn Tyr Ala Gly Phe Gly Val Tyr Thr Phe Asp Trp
            35                  40                  45

Pro Gly His Gly Lys Ser Pro Gly Lys Arg Gly His Thr Ser Val Glu
            50                  55                  60

Glu Ala Met Glu Ile Ile Asp Ser Ile Glu Glu Ile Arg Glu Lys
65                  70                  75                  80

Pro Phe Leu Phe Gly His Ser Leu Gly Gly Leu Thr Val Ile Arg Tyr
                85                  90                  95

Ala Glu Thr Arg Pro Asp Lys Ile Arg Gly Leu Ile Ala Ser Ser Pro
            100                 105                 110

Ala Leu Ala Lys Ser Pro Glu Thr Pro Gly Phe Met Val Ala Leu Ala
            115                 120                 125

Lys Phe Leu Gly Lys Ile Ala Pro Gly Val Val Leu Ser Asn Gly Ile
130                 135                 140

Lys Pro Glu Leu Leu Ser Arg Asn Arg Asp Ala Val Arg Arg Tyr Val
145                 150                 155                 160

Glu Asp Pro Leu Val His Asp Arg Ile Ser Ala Lys Leu Gly Arg Ser
            165                 170                 175

Ile Phe Val Asn Met Glu Leu Ala His Arg Glu Ala Asp Lys Ile Lys
            180                 185                 190

Val Pro Ile Leu Leu Ile Gly Thr Gly Asp Val Ile Thr Pro Pro
            195                 200                 205

Glu Gly Ser ARg Arg Leu Phe Glu Glu Leu Ala Val Glu Asn Lys Thr
            210                 215                 220

Leu Arg Glu Phe Glu Gly Ala Tyr His Glu Ile Phe Glu Asp Pro Glu
225                 230                 235                 240

Trp Ala Glu Glu Phe His Glu Thr Ile Val Lys Trp Leu Val Glu Lys
```

245                250                255

Ser Tyr Ser Ser Ala Gln
                260

(2) INFORMATION FOR SEQ ID NO:39:

(i) SEQUENCE CHARACTERISTICS:
        (A) LENGTH: 249 AMINO ACIDS
        (B) TYPE: AMINO ACID
        (D) TOPOLOGY: LINEAR (ii) MOLECULE TYPE: PROTEIN (xi) SEQUENCE DESCRIPTION: SEQ ID NO:39:

Leu Ile Gly Asn Leu Lys Leu Lys Arg Phe Glu Glu Val Asn Leu Val
 1               5                  10                  15

Leu Ser Gly Gly Ala Ala Lys Gly Ile Ala His Ile Gly Val Leu Lys
            20                  25                  30

Ala Leu Glu Glu Leu Gly Ile Lys Val Lys Arg Leu Ser Gly Val Ser
        35                  40                  45

Ala Gly Ala Ile Val Ser Val Phe Tyr Ala Ser Gly Tyr Thr Pro Asp
    50                  55                  60

Glu Met Leu Lys Leu Leu Lys Glu Val Asn Trp Leu Lys Leu Phe Lys
65                  70                  75                  80

Phe Lys Thr Pro Lys Met Gly Leu Met Gly Trp Glu Lys Ala Ala Glu
                85                  90                  95

Phe Leu Glu Lys Glu Leu Gly Val Lys Arg Leu Glu Asp Leu Asn Ile
            100                 105                 110

Pro Thr Tyr Leu Cys Ser Ala Asp Leu Tyr Thr Gly Lys Ala Leu Tyr
        115                 120                 125

Phe Gly Arg Gly Asp Leu Ile Pro Val Leu Gly Ser Lys Ser Ile
    130                 135                 140

Pro Gly Ile Phe Glu Pro Val Glu Tyr Glu Asn Phe Leu Leu Val Asp
145                 150                 155                 160

Gly Gly Ile Val Asn Asn Leu Pro Val Glu Pro Leu Glu Lys Phe Lys
                165                 170                 175

Glu Pro Ile Ile Gly Val Asp Val Leu Pro Ile Thr Gln Glu Arg Lys
            180                 185                 190

Ile Lys Asn Ile Leu His Ile Leu Ile Arg Ser Phe Phe Leu Ala Val
        195                 200                 205

Arg SEr Asn Ser Glu Lys Arg Lys Glu Phe Cys Asn Val Val Ile Glu
    210                 215                 220

Pro Pro Leu Glu Glu Phe Ser Pro Leu Asp Val Asn Lys Ala Asp Glu
225                 230                 235                 240

Ile Phe Cys Gly Asp Met Arg Ala Leu
                245

(2) INFORMATION FOR SEQ ID NO:40:

(i) SEQUENCE CHARACTERISTICS:
        (A) LENGTH: 338 AMINO ACIDS
        (B) TYPE: AMINO ACID
        (D) TOPOLOGY: LINEAR (ii) MOLECULE TYPE: PROTEIN (xi) SEQUENCE DESCRIPTION: SEQ ID NO:40:

Met Pro Ala Asn Asp Ser Pro Thr Ile Asp Phe Asn Pro Arg Gly Ile
 1               5                  10                  15

-continued

```
Leu Arg Asn Ala His Ala Gln Val Ile Leu Ala Thr Ser Gly Leu Arg
             20                  25                  30

Lys Ala Phe Leu Lys Arg Thr His Lys Ser Tyr Leu Ser Thr Ala Gln
         35                  40                  45

Trp Leu Glu Leu Asp Ala Gly Asn Gly Val Thr Leu Ala Gly Glu Leu
     50                  55                  60

Asn Thr Ala Pro Ala Thr Ala Ser Ser His Pro Ala His Lys Asn
 65                  70                  75                  80

Thr Leu Val Ile Val Leu His Gly Trp Glu Gly Ser Ser Gln Ser Ala
                 85                  90                  95

Tyr Ala Thr Ser Ala Gly Ser Thr Leu Phe Asp Asn Gly Phe Asp Thr
                100                 105                 110

Phe Arg Leu Asn Phe Arg Asp His Gly Asp Thr Tyr His Leu Asn Arg
            115                 120                 125

Gly Ile Phe Asn Ser Ser Leu Ile Asp Glu Val Val Gly Ala Val Lys
    130                 135                 140

Ala Ile Gln Gln Gln Thr Asp Tyr Asp Lys Tyr Cys Leu Met Gly Phe
145                 150                 155                 160

Ser Leu Gly Gly Asn Phe Ala Leu Arg Val Ala Val Arg Glu Gln His
                165                 170                 175

Leu Ala Lys Pro Leu Ala Gly Val Leu Ala Val Cys Pro Val Leu Asp
            180                 185                 190

Pro Ala His Thr Met Met Ala Leu Asn Arg Gly Ala Phe Phe Tyr Gly
        195                 200                 205

Arg Tyr Phe Ala His Lys Trp Lys Arg Ser Leu Thr Ala Lys Leu Ala
    210                 215                 220

Ala Phe Pro Asp Tyr Lys Tyr Gly Lys Asp Leu Lys Ser Ile His Thr
225                 230                 235                 240

Leu Asp Glu Leu Asn Asn Tyr Phe Ile Pro Arg Tyr Thr Gly Phe Asn
                245                 250                 255

Ser Val Ser Glu Tyr Phe Lys Ser Tyr Thr Leu Thr Gly Gln Lys Leu
            260                 265                 270

Ala Phe Leu Asn Cys Pro Ser Tyr Ile Leu Ala Ala Gly Asp Asp Pro
        275                 280                 285

Ile Ile Pro Ala Ser Asp Phe Gln Lys Ile Ala Lys Pro Ala Asn Leu
    290                 295                 300

His Ile Thr Val Thr Gln Gln Gly Ser His Cys Ala Tyr Leu Glu Asn
305                 310                 315                 320

Leu His Lys Pro Ser Ala Ala Asp Lys Tyr Ala Val Lys Leu Phe Gly
                325                 330                 335

Ala Cys
```

(2) INFORMATION FOR SEQ ID NO:41:

(i) SEQUENCE CHARACTERISTICS:
      (A) LENGTH: 311 AMINO ACIDS
      (B) TYPE: AMINO ACID
      (D) TOPOLOGY: LINEAR (ii) MOLECULE TYPE: PROTEIN (xi) SEQUENCE DESCRIPTION: SEQ ID NO:41:

```
Met Leu Asp Met Pro Ile Asp Pro Val Tyr Tyr Gln Leu Ala Glu Tyr
 1               5                  10                  15

Phe Asp Ser Leu Pro Lys Phe Asp GLn Phe Ser Ser Ala Arg Glu Tyr
             20                  25                  30
```

```
Arg Glu Ala Ile Asn Arg Ile Tyr Glu Arg Asn Arg Gln Leu Ser
        35                  40                  45

Gln His Glu Arg Val Glu Arg Val Glu Asp Arg Thr Ile Lys Gly Arg
        50                  55                  60

Asn Gly Asp Ile Arg Val Arg Val Tyr Gln Gln Lys Pro Asp Ser Pro
65                  70                  75                  80

Val Leu Val Tyr Tyr His Gly Gly Phe Val Ile Cys Ser Ile Glu
                85                  90                  95

Ser HIs Asp Ala Leu Cys Arg ARg Ile Ala Arg Leu Ser Asn Ser Thr
                100                 105                 110

Val Val Ser Val Asp Tyr Arg Leu Ala Pro Glu His Lys Phe Pro Ala
                115                 120                 125

Ala Val Tyr Asp Cys Tyr Asp Ala Thr Lys Trp Val Ala Glu Asn Ala
        130                 135                 140

Glu Glu Leu Arg Ile Asp Pro Ser Lys Ile Phe Val Gly Gly Asp Ser
145                 150                 155                 160

Ala Gly Gly Asn Leu Ala Ala Ala Val Ser Ile Met Ala Arg Asp Ser
                165                 170                 175

Gly Glu Asp Phe Ile Lys His Gln Ile Leu Ile Tyr Pro Val Val Asn
                180                 185                 190

Phe Val Ala Pro Thr Pro Ser Leu Leu Glu Phe GLy Glu Gly Leu Trp
        195                 200                 205

Ile Leu Asp Gln Lys Ile Met Ser Trp Phe Ser Glu Gln Tyr Phe Ser
210                 215                 220

Arg Glu Glu Asp Lys Phe Asn Pro Leu Ala Ser Val Ile Phe Ala Asp
225                 230                 235                 240

Leu Glu Asn Leu Pro Pro Ala Leu Ile Ile Thr Ala Glu Tyr Asp Pro
                245                 250                 255

Leu Arg Asp Glu Gly Glu Val Phe Gly Gln Met Leu Arg Arg Ala Gly
                260                 265                 270

Val Glu Ala Ser Ile Val Arg Tyr Arg Gly Val Leu His Gly Phe Ile
        275                 280                 285

Asn Tyr Tyr Pro Val Leu Lys Ala Ala Arg Asp Ala Ile Asn Gln Ile
290                 295                 300

Ala Ala Leu leu Val Phe Asp
305                 310

(2) INFORMATION FOR SEQ ID NO:42:

(i) SEQUENCE CHARACTERISTICS:
        (A) LENGTH: 305 AMINO ACIDS
        (B) TYPE: AMINO ACID
        (D) TOPOLOGY: LINEAR (ii) MOLECULE TYPE: PROTEIN (xi) SEQUENCE DESCRIPTION: SEQ ID NO:42:

Met Pro Leu Asp Pro Arg Ile Lys Lys Leu Leu Glu Ser Ala Leu Thr
                5                   10                  15

Ile Pro Ile Gly Lys Ala Pro Val Glu Val Arg Lys Ile Phe Arg
                20                  25                  30

Gln Leu Ala Ser Ala Ala Pro Lys Val Glu Val Gly Lys Val Glu Asp
        35                  40                  45

Ile Lys Ile Pro Gly Ser Glu Thr Val Ile Asn Ala Arg Val Tyr Phe
        50                  55                  60

Pro Lys Ser Ser Gly Pro Tyr Gly Val Leu Val Tyr Leu His Gly Gly
65                  70                  75                  80
```

```
Gly Phe Val Ile Gly Asp Val Glu Ser Tyr Asp Pro Leu Cys Arg Ala
                85              90              95
Ile Thr Asn Ala Cys Asn Cys Val Val Val Ser Val Asp Tyr Arg Leu
            100             105             110
Ala Pro Glu Tyr Lys Phe Pro Ser Ala Val Ile Asp Ser Phe Asp Ala
            115             120             125
Thr Asn Trp Val Tyr Asn Asn Leu Asp Lys Phe Asp Gly Lys Met Gly
            130             135             140
Val Ala Ile Ala Gly Asp Ser Ala Gly Gly Asn Leu Ala Ala Val Val
145             150             155             160
Ala Leu Leu Ser Lys Gly Lys Ile Asn Leu Lys Tyr Gln Ile Leu Val
            165             170             175
Tyr Pro Ala Val Ser Leu Asp Asn Val Ser Arg Ser Met Ile Glu Tyr
            180             185             190
Ser Asp Gly Phe Phe Leu Thr Arg Glu His Ile Glu Trp Phe Gly Ser
        195             200             205
Gln Tyr Leu Arg Ser Pro Ala Asp Leu Leu Asp Phe Arg Phe Ser Pro
    210             215             220
Ile Leu Ala Gln Asp Phe Asn Gly Leu Pro Pro Ala Leu Ile Ile Thr
225             230             235             240
Ala Glu Tyr Asp Pro Leu Arg Asp Gln Gly Glu Ala Tyr Ala Asn Lys
            245             250             255
Leu Leu Gln Ala Gly Val Ser Val Thr Ser Val Arg Phe Asn Asn Val
            260             265             270
Ile His Gly Phe Leu Ser Phe Phe Pro Leu Met Glu Gln Gly Arg Asp
            275             280             285
Ala Ile Gly Leu Ile Gly Ser Val Leu Arg Arg Val Phe Tyr Asp Lys
            290             295             300
Ile
305
```